United States Patent [19]
Hlavka et al.

[11] Patent Number: 5,281,628
[45] Date of Patent: Jan. 25, 1994

[54] 9-AMINO-7-(SUBSTITUTED)-6-DEMETHYL-6-DEOXYTETRACYCLINES

[75] Inventors: Joseph J. Hlavka, Tuxedo Park; Phaik-Eng Sum, Pomona, both of N.Y.; Yakov Gluzman, Upper Saddle River, N.J.; Ving J. Lee, Monsey, N.Y.

[73] Assignee: American Cyanamid Company, Wayne, N.J.

[21] Appl. No.: 771,697

[22] Filed: Oct. 4, 1991

[51] Int. Cl.$^5$ ............... A01N 37/00; C07C 103/19; C09B 1/29
[52] U.S. Cl. ............... 514/510; 514/577; 514/619; 552/205; 552/226
[58] Field of Search ............... 552/205, 226; 514/510, 514/577, 619

[56] References Cited

U.S. PATENT DOCUMENTS

| | | | |
|---|---|---|---|
| Re. 26,253 | 8/1967 | Petisi | 552/205 |
| Re. 26,271 | 9/1967 | Boothe et al. | 552/205 |
| 2,482,055 | 9/1949 | Duggar | 552/205 |
| 2,997,471 | 8/1961 | Cheney et al. | 552/205 |
| 3,007,965 | 11/1961 | Growich | 552/205 |
| 3,043,875 | 7/1962 | Beereboom | 552/205 |
| 3,200,149 | 8/1965 | Blackwood | 552/205 |
| 3,226,436 | 12/1965 | Petisi | 552/205 |
| 3,338,963 | 8/1967 | Petisi et al. | 552/205 |
| 3,341,585 | 9/1967 | Bitha | 552/205 |
| 3,360,557 | 12/1967 | Shu | 552/205 |
| 3,3,60,561 | 12/1967 | Zambrano | 552/205 |
| 3,518,306 | 6/9170 | Martell | 552/205 |
| 5,021,407 | 6/1991 | Levy | 514/154 |

OTHER PUBLICATIONS

Chopra, Handbook of Experimental Pharmacology, vol. 78, 317–392, Springer-Verlag (1985).
Levy, Antimicrobial Agents and Chemotherapy, vol. 33, No. 8, 1373–1374, (Aug. 1989).
Salyers, Molecular Microbiology, 4(1), 151–156 (1990).

*Primary Examiner*—C. Warren Ivy
*Assistant Examiner*—Raymond Covington
*Attorney, Agent, or Firm*—Thomas S. Szatkowski

[57] ABSTRACT

9-amino-7-(substituted amino)-6-demethyl-6-deoxytetracyclines having activity against a wide spectrum of organisms including organisms which are resistant to tetracyclines are disclosed. Also disclosed are intermediates and methods for making the novel compounds of the present invention.

40 Claims, No Drawings

9-AMINO-7-(SUBSTITUTED)-6-DEMETHYL-6-DEOXYTETRACYCLINES

FIELD OF THE INVENTION

The invention relates to novel [4S-(4α,12α)]-9-amino-4-(dimethylamino)-7-(substituted amino)-1,4,4a,5-,5a,6,11,12a-octahydro-3,10,12,12a-tetrahydroxy-1,11-dioxo-2-naphthacenecarboxamides, hereinafter called 9-amino-7-(substituted amino)-6-demethyl-6-deoxytetracyclines, which exhibit antibiotic activity against a wide spectrum of organisms including organisms which are resistant to tetracyclines and are useful as antibacterial agents.

The invention also relates to novel 7-(substituted amino)-9-nitro-6-demethyl-6-deoxytetracycline compounds useful for making the novel compounds of the present invention and to novel methods for producing the novel compounds and intermediate compounds.

DESCRIPTION OF THE PRIOR ART

A variety of tetracycline antibiotics have been synthesized and described for the treatment of infectious diseases in man and animals since 1947. Tetracyclines inhibit protein synthesis by binding to the 30S subunit of the bacterial ribosome preventing binding of aminoacyl RNA (Chopra, Handbook of Experimental Pharmacology, Vol. 78, 317-392, Springer-Verlag, 1985). Resistance to tetracyclines has emerged among many clinically important microorganisms which limit the utility of these antibiotics. There are two major mechanisms of bacterial resistance to tetracyclines: a) energy-dependent efflux of the antibiotic mediated by proteins located in the cytoplasmic membrane which prevents intracellular accumulation of tetracycline (S. B. Levy, et al., Antimicrob. Agents Chemotherapy 33, 1373-1374 (1989); and b) ribosomal protection mediated by a cytoplasmic protein which interacts with the ribosome such that tetracycline no longer binds or inhibits protein synthesis (A. A. Salyers, B. S. Speers and N. B. Shoemaker, Mol. Microbiol, 4:151-156, 1990). The efflux mechanism of resistance is encoded by resistance determinants designated tetA-tetL. They are common in many Gram-negative bacteria (resistance genes Class A-E), such as Enterobacteriaceae, Pseudomonas, Haemoohilus and Aeromonas, and in Gram-positive bacteria (resistance genes Class K and L), such as Staphylococcus, Bacillus and Streptococcus. The ribosomal protection mechanism of resistance is encoded by resistance determinants designated TetM, N and O, and is common in Staphylococcus, Streptococcus, Campylobacter, Gardnerella, Haemoohilus and Mycoolasma (A. A. Salyers, B. S. Speers and N. B. Shoemaker, Mol. Microbiol, 4:151-156 1990).

A particularly useful tetracycline compound is 7-(dimethylamino)-6-demethyl-6-deoxytetracycline, known as minocycline (see U.S. Pat. Nos. 3,148,212, 26,253 and 3,226,436 discussed below). However, strains harboring the tetB (efflux in gram-negative bacteria) mechanism, but not tetK (efflux in Staphylococcus) are resistant to minocycline. Also, strains carrying tetM (ribosomal protection) are resistant to minocycline. This invention describes the synthesis of novel tetracycline compounds which demonstrate significant in vitro and in vivo activity vs. tetracycline and minocycline susceptible strains and some tetracycline and minocycline resistant strains, that is, those harboring the tetM (ribosomal protection) resistance determinants.

Duggar, U.S. Pat. No. 2,482,055, discloses the preparation of Aureomycin® (I) by fermentation which have antibacterial activity. Growich et al., U.S. Pat. No. 3,007,965, disclose improvements to the fermentation preparation of I. Neither of these patents teaches or suggests the 6-demethyl-6-deoxytetracyclines

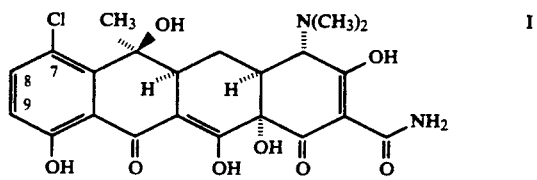

Beereboom et al., U.S. Pat. No. 3,043,875 discloses tetracycline derivatives of the formulae (II) and (III) where R is H or CH₃; R₁ is H and when R is CH₃; OH; R₂ is H and N(CH₃)₂; X and Y are halogen; Z is H and halogen and B is bromo, chloro and iodo, which have antibacterial activity. This patent does not teach or suggest the inclusion of both di(lower alkyl)amino or mono(lower alkyl)amino substituents (at Y or Z) and an amino function (at B).

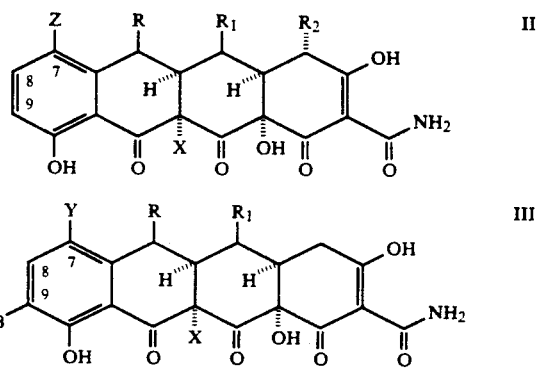

Boothe et al., U.S. Pat. No. 3,148,212, reissued as U.S. Pat. No. 26,253, and Petisi et al., U.S. Pat. No. 3,226,436, discloses tetracycline derivatives of the formula (IV) wherein R is hydrogen or methyl and R₁ and R₂ is hydrogen, mono(lower alkyl)amino or di(lower alkyl)amino with the proviso that R₁ and R₂ cannot both be hydrogen, which are useful for treating bacterial infections. This patent does not teach or suggest the inclusion of a 9-amino functionality (at R₂).

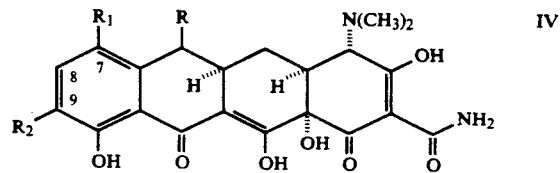

Blackwood et al., U.S. Pat. No. 3,200,149 discloses tetracycline derivatives of the formulae (V) and (VI) and reduction products thereof wherein Y may be hydrogen or hydroxyl, X may be hydrogen, chloro, iodo, or bromo, X₁ may be hydrogen, amino, and lower alkanoylamino, X₂ may be hydrogen or nitro and Z is chloro or fluoro which possess microbiological activity. This patent does not teach or suggest the inclusion of both a di(lower alkyl)amino group (at X) and another nitrogen functionality (at $X_1$) on the 6-demethyl-6-deoxytetracycline nucleus.

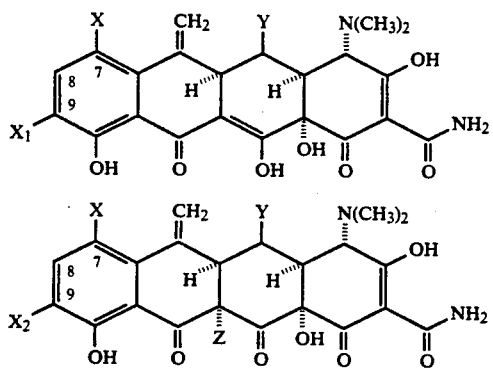

Petisi et al., U.S. Pat. No. 3,338,963 discloses tetracycline compounds of the formula (VII) wherein $R_1$ and $R_2$ are hydrogen, nitro, amino, formylamino, acetylamino, p-(dihydroxyboryl)benzoylamino, p-(aminobenzenesulfonyl)amino, chlorine, bromine or diazonium with the proviso that $R_1$ and $R_2$ may not both be hydrogen and with the further proviso that when $R_1$ is chlorine or bromine, R may not be hydrogen and vice versa, $R_3$ is hydrogen or methyl and $R_4$ is hydrogen or hydroxy, which have broad-spectrum antibacterial activity. This patent does not teach or suggest the inclusion of both di(lower alkyl)amino or mono(lower alkyl)amino substituents (at $R_1$) and amino substituents (at $R_2$).

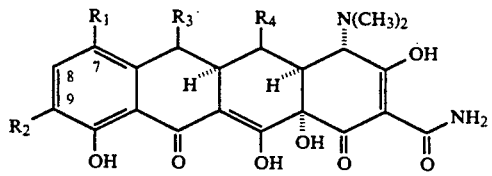

Bitha et al., U.S. Pat. No. 3,341,585 discloses tetracycline compounds of the formula (VIII) wherein $R_5$ is hydrogen, α-hydroxy or α-hydroxy, $R_6$ is α-methyl or α-methyl, and $R_7$ and $R_9$ are each hydrogen, mono(-lower alkyl)amino or di(lower alkyl)amino with the proviso that $R_7$ and $R_9$ cannot both be hydrogen and with the further proviso that when $R_5$ is hydrogen then $R_6$ is β-methyl. A preferred embodiment of the general formula (VIII) is when $R_5$ is α-hydroxy or β-hydroxy, $R_6$ is α-methyl or β-methyl, $R_7$ is di(lower alkyl)amino and $R_9$ is hydrogen, which have broad-spectrum antibacterial activity This patent does not teach or suggest the inclusion of both di(lower alkyl)amino or mono(-lower alkyl)amino substituents (at $R_7$) and amino substituents (at $R_9$).

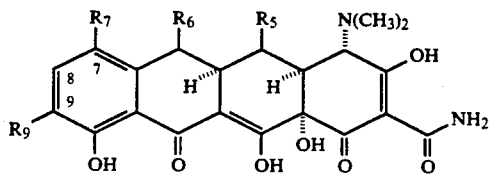

Shu, U.S. Pat. No. 3,360,557 discloses 9-hydroxytetracyclines of the formula (IX) wherein $R_1$ is hydrogen or hydroxy, $R_2$ is hydrogen or hydroxy, $R_3$ is hydrogen or methyl, $R_2$ and $R_3$ taken together is methylene, and $R_4$ is hydrogen, halogen, nitro, amino, mono(lower alkyl)amino or di(lower alkyl)amino, which have been found to possess antibacterial activity. This patent is restricted to 9-hydroxytetracyclines and does not teach or suggest the presently claimed compounds.

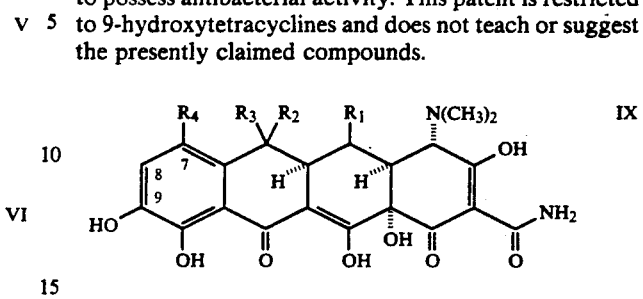

Zambrano, U.S. Pat. No. 3,360,561 discloses a process for preparing 9-nitrotetracyclines of the formula (X) wherein $R_5$ is hydrogen or hydroxy, $R_1$ is hydrogen or hydroxy, $R_6$ is hydrogen or methyl, $R_1$ and $R_6$ taken together is methylene, $R_7$ is hydrogen, chloro or nitro and $R_9$ is hydrogen or nitro with the proviso that $R_7$ and $R_9$ cannot both be hydrogen. This patent does not teach or suggest the inclusion of both a di(lower alkyl)amino or mono(lower alkyl)amino substituent (at $R_7$) and an amino functionality (at $R_9$).

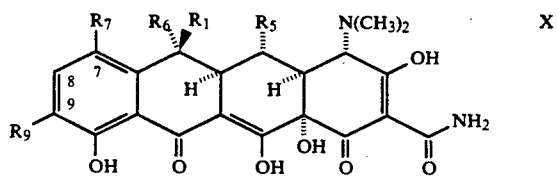

Martell et al., U.S. Pat. No. 3,518,306 discloses 7-and/or 9-(N-nitrosoalkylamino)-6-demethyl-6-deoxytetracyclines of the formula (XI) which possess in vivo antibacterial activity. This patent does not teach or suggest the inclusion of both a di(lower alkyl)amino or mono(lower alkyl)amino substituent (at C-7) and an amino functionality (at C-9).

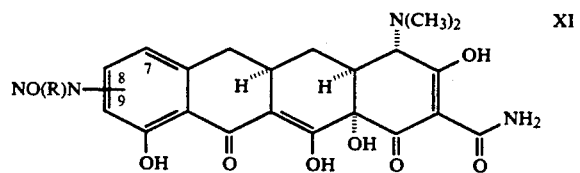

In U.S. Pat. No. 5,021,407, a method of overcoming the resistance of tetracycline resistant bacteria is disclosed. The method involves utilizing a blocking agent compound in conjunction with a tetracycline type antibiotic. This patent does not disclose novel tetracycline compounds which themselves have activity against resistant organisms.

In summary, none of the above patents teach or suggest the novel compounds of this application. In addition, none of the above patents teach or suggest novel tetracycline compounds having activity against tetracycline and minocycline resistant strains as well as strains which are normally susceptible to tetracyclines.

SUMMARY OF THE INVENTION

This invention is concerned with novel 9-amino-7-(substituted amino)-6-demethyl-6-deoxytetracyclines, represented by formula I and II, which have antibacterial activity, with methods of treating infectious diseases in warm-blooded animals employing these new compounds; with methods of treating or controlling veterinary diseases; with pharmaceutical preparations containing these compounds; with novel intermediate compounds and processes for the production of these compounds. More particularly, this invention is concerned with compounds of formula I which have enhanced in vitro and in vivo antibacterial activity against tetracycline resistant strains as well as a high level of activity against strains which are normally susceptible to tetracyclines.

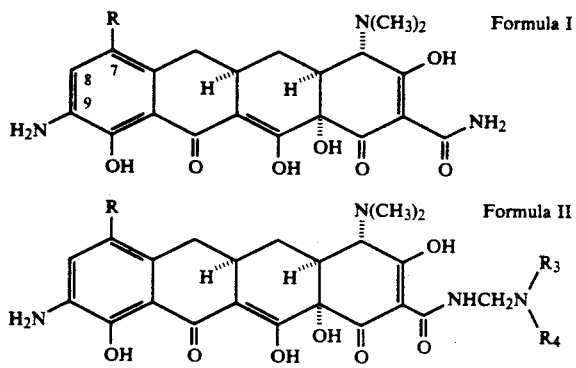

In formula I and II, $R=NR_1R_2$, and when $R_1=$hydrogen, $R_2=$methyl, ethyl, n-propyl, 1-methylethyl, n-butyl, 1-methylpropyl, 2-methylpropyl or 1,1-dimethylethyl; and when $R_1=$methyl or ethyl, $R_2=$methyl, ethyl, n-propyl, 1-methylethyl, n-butyl, 1-methylpropyl or 2-methylpropyl; and when $R_1=$n-propyl, $R_2=$n-propyl, 1-methylethyl, n-butyl, 1-methylpropyl or 2-methylpropyl; and when $R_1=$1-methylethyl, $R_2=$n-butyl, 1-methylpropyl or 2-methylpropyl; and when $R_1=$n-butyl, $R_2=$n-butyl, 1-methylpropyl or 2-methylpropyl; and when $R_1=$1-methylpropyl, $R_2=$2-methylpropyl; $R_3$ is selected from hydrogen, straight or branched ($C_1$–$C_3$)alkyl group such as methyl, ethyl, n-propyl or 1-methylethyl; ($C_6$–$C_{10}$)aryl group such as phenyl, α-naphthyl or β-naphthyl; ($C_7$—$C_9$)aralkyl group such as benzyl, 1-phenylethyl, 2-phenylethyl or phenylpropyl; a heterocycle group such as 2 or 3-furanyl, 2 or 3-thienyl, 2,3 or 4-pyridyl, di($C_1$–$C_3$)alkyl substituted pyridyl, benzofuranyl, benzothienyl, quinolinyl or —(CH$_2$)nCOOR$_5$ when n=1–4 and R$_5$ is selected from hydrogen; straight or branched ($C_1$–$C_3$)alkyl group such as methyl, ethyl, n-propyl or 1-methylethyl; or ($C_6$–$C_{10}$) aryl group such as phenyl, α-naphthyl, β-naphthyl; R$_4$ is selected from hydrogen; straight or branched ($C_1$–$C_3$)alkyl group such as methyl, ethyl, n-propyl or 1-methylethyl; ($C_6$–$C_{10}$)aryl group such as phenyl, α-naphthyl or β-naphthyl; ($C_7$–$C_9$)aralkyl group such as benzyl, 1-phenylethyl, 2-phenylethyl or phenylpropyl; a heterocycle group such as 2 or 3-furanyl, 2 or 3-thienyl, 2,3 or 4-pyridyl, di($C_1$–$C_3$)alkyl substituted pyridyl, benzofuranyl, benzothienyl, quinolinyl or —(CH$_2$)$_n$COOR$_6$ when n=1–4 and R$_6$ is selected from hydrogen; straight or branched ($C_1$–$C_3$)alkyl such as methyl, ethyl, n-propyl or 1-methylethyl; or ($C_6$–$C_{10}$)aryl such as phenyl, α-naphthyl or β-naphthyl; or R$_3$ and R$_4$ taken together are —(CH$_2$)$_2$W(CH$_2$)— wherein W is selected from (CH$_2$)$_n$ and n=0–1, —NH, —N($C_1$–$C_3$)alkyl, —N($C_1$–$C_4$)alkoxy, oxygen, sulfur or substituted congeners selected from (L or D) proline, ethyl (L or D) prolinate, morpholine, pyrrolidine or piperidine; and the pharmacologically acceptable organic and inorganic salts, and metal complexes.

Particularly preferred are compounds according to the above formula I and II in which $R=NR_1R_2$, and when $R_1=$hydrogen, $R_2=$ethyl, n-propyl, 1-methylethyl, n-butyl, 1-methylpropyl, 2-methylpropyl or 1,1-dimethylethyl; and when $R_1=$methyl, $R_2=$methyl, ethyl, n-propyl, n-butyl, 1-methylpropyl or 2-methylpropyl; and when $R_1=$ethyl, $R_2=$ethyl, n-propyl, n-butyl or 2-methylpropyl; and when $R_1=$n-propyl, $R_2=$n-propyl, n-butyl or 2-methylpropyl; and when $R_1=$n-butyl, $R_2=$n-butyl or 2-methylpropyl; $R_3$ is selected from hydrogen, straight or branched ($C_1$–$C_3$)alkyl group such as methyl, ethyl, n-propyl or 1-methylethyl; ($C_6$–$C_{10}$)aryl group such as phenyl, α-naphthyl or β-naphthyl; ($C_7$–$C_9$)aralkyl group such as benzyl, 1-phenylethyl, 2-phenylethyl or phenylpropyl; a heterocycle group such as 2 or 3-furanyl, 2 or 3-thienyl, 2,3 or 4-pyridyl, di($C_1$–$C_3$)alkyl substituted pyridyl, benzofuranyl, benzothienyl, quinolinyl or —(CH$_2$)$_n$COOR$_5$ when n=1–4 and R$_5$ is selected from hydrogen; straight or branched ($C_1$–$C_3$)alkyl group such as methyl, ethyl, n-propyl or 1-methylethyl; or ($C_6$–$C_{10}$) aryl group such as phenyl, α-naphthyl, β-naphthyl; R$_4$ is selected from hydrogen; straight or branched ($C_1$–$C_3$)alkyl group such as methyl, ethyl, n-propyl or 1-methylethyl; ($C_6$–$C_{10}$)aryl group such as phenyl, α-naphthyl or β-naphthyl; ($C_7$–$C_9$)aralkyl group such as benzyl, 1-phenylethyl, 2-phenylethyl or phenylpropyl; a heterocycle group such as 2 or 3-furanyl, 2 or 3-thienyl, 2,3 or 4-pyridyl, di($C_1$–$C_3$)alkyl substituted pyridyl, benzofuranyl, benzothienyl, quinolinyl or —(CH$_2$)$_n$COOR$_6$ when n=1–4 and R$_6$ is selected from hydrogen; straight or branched ($C_1$–$C_3$)alkyl such as methyl, ethyl, n-propyl or 1-methylethyl; or )aryl such as phenyl, α-naphthyl or β-naphthyl; or R$_3$ and R$_4$ taken together are —(CH$_2$)$_2$W(CH$_2$)—, wherein W is selected from (CH$_2$)$_n$ and n=0–1, —NH, —N($C_1$–$C_3$)alkyl, —N($C_1$–$C_4$)alkoxy, oxygen, sulfur or substituted congeners selected from (L or D) proline, ethyl (L or D) prolinate, morpholine, pyrrolidine or piperidine; and the pharmacologically acceptable organic and inorganic salts, and metal complexes.

Most particularly preferred are compounds according to the above formula I and II in which $R=NR_1R_2$, and when $R_1=$hydrogen, $R_2=$ethyl, n-propyl or 1-methylethyl; and when $R_1=$methyl, $R_2=$methyl, ethyl or n-propyl; and when $R_1=$ethyl, $R_2=$ethyl; $R_3$ is selected from hydrogen, straight or branched ($C_1$–$C_3$)alkyl group such as methyl, ethyl, n-propyl or 1-methylethyl; ($C_6$–$C_{10}$)aryl group such as phenyl, α-naphthyl or β-naphthyl; ($C_7$–$C_9$)aralkyl group such as benzyl, 1-phenylethyl, 2-phenylethyl or phenylpropyl; a heterocycle group such as 2 or 3-furanyl, 2 or 3-thienyl, 2,3 or 4-pyridyl, di($C_1$–$C_3$)alkyl substituted pyridyl, benzofuranyl, benzothienyl, quinolinyl or —(CH$_2$_nCOOR$_5$ when n=1–4 and R$_5$ is selected from hydrogen; straight or branched (C alkyl group such as methyl, ethyl, n-propyl or 1-methylethyl; or ($C_6$–$C_{10}$) aryl group such as phenyl, α-naphthyl, β-naphthyl; R$_4$ is selected from hydrogen; straight or branched ($C_1$–$C_3$)alkyl group such as methyl, ethyl, n-propyl or 1-methylethyl; ($C_6$–$C_{10}$)aryl group such as phenyl, α-naphthyl or β-naphthyl; ($C_7$–$C_9$)aralkyl group such as benzyl, 1-phenylethyl, 2-phenylethyl or phenylpropyl; a heterocycle group such as 2 or 3-furanyl, 2 or 3-thienyl, 2,3 or 4-pyridyl, di($C_1$–$C_3$)alkyl substituted pyridyl, benzofuranyl, benzothienyl, quinolinyl or —(CH$_2$)$_n$COOR$_6$ when n=1-4 and R$_6$ is selected from hydrogen; straight or branched (C )alkyl such as methyl, ethyl, n-propyl or 1-methylethyl: or (C$_6$-C$_{10}$)aryl such as phenyl, α-naphthyl or β-naphthyl; or R$_3$ and R$_4$ taken together are —(CH$_2$)$_2$W(CH$_2$)—, wherein W is selected from (CH$_2$)$_n$ and n=0-1, —NH, —N(C$_1$-C$_3$)alkyl, —N(C$_1$-C$_4$)alkoxy, oxygen, sulfur or substituted congeners selected from (L or D) proline, ethyl (L or D) prolinate, morpholine, pyrrolidine or piperidine; and the pharmacologically acceptable organic and inorganic salts, and metal complexes.

Also included in the present invention are compounds useful as intermediate for producing the above compounds of formula I. Such intermediate compounds include those having the formulae:

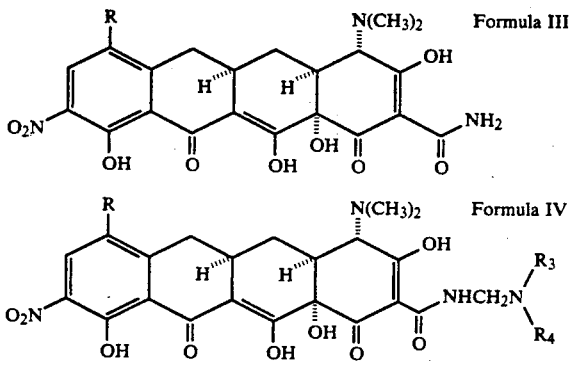

wherein: R=NR$_1$R$_2$, and when R$_1$=hydrogen, R$_2$,=methyl, ethyl, n-propyl, 1-methylethyl, n-butyl, 1-methylpropyl, 2-methylpropyl or 1,1-dimethylethyl; and when R$_1$=methyl or ethyl, R$_2$=methyl, ethyl, n-propyl, 1-methylethyl, n-butyl, 1-methylpropyl or 2-methylpropyl; and when R$_1$=n-propyl, R$_2$=n-propyl, 1-methylethyl, n-butyl, 1-methylpropyl or 2-methylpropyl; and when R$_1$=1-methylethyl, R$_2$=n-butyl, 1-methylpropyl or 2-methylpropyl; and when R$_1$=n-butyl, R$_2$=n-butyl, 1-methylpropyl or 2-methylpropyl; and when R$_1$=1-methylpropyl, R$_2$=2-methylpropyl; R$_3$ is selected from hydrogen, straight or branched ($_1$-C$_3$)alkyl group such as methyl, ethyl, n-propyl or 1-methylethyl; (C$_6$-C$_{10}$)aryl group such as phenyl, α-naphthyl or β-naphthyl; (C$_7$C$_9$)aralkyl group such as benzyl, 1-phenylethyl, 2-phenylethyl or phenylpropyl; a heterocycle group such as 2 or 3-furanyl, 2 or 3-thienyl, 2,3 or 4-pyridyl, di(C$_1$-C$_3$)alkyl substituted pyridyl, benzofuranyl, benzothienyl, quinolinyl or —(CH$_2$$_n$COOR$_5$ when n=1-4 and R$_5$ is selected from hydrogen; straight or branched (C$_1$-C$_3$)alkyl group such as methyl, ethyl, n-propyl or 1-methylethyl; or (C$_6$-C$_{10}$) aryl group such as phenyl, α-naphthyl, β-naphthyl; R$_4$ is selected from hydrogen; straight or branched (C$_1$-C$_3$)alkyl group such as methyl, ethyl, n-propyl or 1-methylethyl; (C$_7$-C$_9$)aryl group such as phenyl, α-naphthyl or β-naphthyl; (C$_7$-C$_9$)aralkyl group such as benzyl, 1-phenylethyl, 2-phenylethyl or phenylpropyl; a heterocycle group such as 2 or 3-furanyl, 2 or 3-thienyl, 2,3 or 4-pyridyl, di(C$_1$-C$_3$)alkyl substituted pyridyl, benzofuranyl, benzothienyl, quinolinyl or —(CH$_2$)$_n$COOR$_6$ when n=1-4 and R$_6$ is selected from hydrogen; straight or branched (C$_1$-C$_3$)alkyl such as methyl, ethyl, n-propyl or 1-methylethyl; or (C$_6$-C$_{10}$)aryl such as phenyl, α-naphthyl or β-naphthyl; or R$_3$ and R$_4$ taken together are —(CH$_2$)$_2$W(CH$_2$)—, wherein W is selected from (CH$_2$)$_n$ and n=0-1, —NH, —N(C$_1$-C$_3$)alkyl, —N(C$_1$-C$_4$)alkoxy, oxygen, sulfur or substituted congeners selected from (L or D) proline, ethyl (L or D) prolinate, morpholine, pyrrolidine or piperidine; and the pharmacologically acceptable organic and inorganic salts, and metal complexes.

Particularly preferred are compounds according to the above formula III and IV in which R=NR$_1$R$_2$, and when R$_1$=hydrogen, R$_2$=ethyl, n-propyl, 1-methylethyl, n-butyl, 1-methylpropyl, 2-methylpropyl or 1,1-dimethylethyl; and when R$_1$=methyl, R$_2$=methyl, ethyl, n-propyl, n-butyl, 1-methylpropyl or 2-methylpropyl; and when R$_1$=ethyl, R$_2$=ethyl, n-propyl, n-butyl or 2-methylpropyl; and when R$_1$=n-propyl, R$_2$=n-propyl, n-butyl or 2-methylpropyl; and when R$_1$=n-butyl, R$_2$=n-butyl or 2-methylpropyl; R$_3$ is selected from hydrogen, straight or branched ($_1$-C$_3$)alkyl group such as methyl, ethyl, n-propyl or 1-methylethyl; (C$_6$-C$_{10}$)aryl group such as phenyl, α-naphthyl or β-naphthyl; (C$_7$-C$_9$)aralkyl group such as benzyl, 1-phenylethyl, 2-phenylethyl or phenylpropyl; a heterocycle group such as 2 or 3-furanyl, 2 or 3-thienyl, 2,3 or 4-pyridyl, di(C$_1$-C$_3$)alkyl substituted pyridyl, benzofuranyl, benzothienyl, quinolinyl or —(CH$_2$)$_n$COOR$_5$ when n=1-4 and R$_5$ is selected from hydrogen; straight or branched (C$_1$-C$_3$)alkyl group such as methyl, ethyl, n-propyl or 1-methylethyl; or (C$_6$-C$_{10}$) aryl group such as phenyl, α-naphthyl, β-naphthyl; R$_4$ is selected from hydrogen; straight or branched (C$_1$-C$_3$)alkyl group such as methyl, ethyl, n-propyl or 1-methylethyl; (C$_6$-C$_{10}$)aryl group such as phenyl, α-naphthyl or β-naphthyl; (C$_7$-C$_9$)aralkyl group such as benzyl, 1-phenylethyl, 2-phenylethyl or phenylpropyl; a heterocycle group such as 2 or 3-furanyl, 2 or 3-thienyl, 2,3 or 4-pyridyl, di(C$_1$-C$_3$)alkyl substituted pyridyl, benzofuranyl, benzothienyl, quinolinyl or —(CH$_2$)$_n$COOR$_6$ when n=1-4 and R$_6$ is selected from hydrogen; straight or branched (C$_1$-C$_3$)alkyl such as methyl, ethyl; n-propyl or 1-methylethyl; or (C$_6$-C$_{10}$)aryl such as phenyl, α-naphthyl or β-naphthyl; or R$_3$ and R$_4$ taken together are —(CH$_2$)$_2$W(CH$_2$)—, wherein W is selected from (CH$_2$)$_n$ and n=0-1, —NH, —N(C )alkyl, —N(C$_1$-C$_4$)alkoxy, oxygen, sulfur or substituted congeners selected from (L or D) proline, ethyl (L or D) prolinate, morpholine, pyrrolidine or piperidine; and the pharmacologically acceptable organic and inorganic salts, and metal complexes.

Most particularly preferred are compounds according to the above formula III and IV in which R=NR$_1$,R$_2$, and when R$_1$=hydrogen, R$_2$=ethyl, n-propyl or 1-methylethyl; and when R$_1$=methyl, R$_2$=methyl, ethyl or n-propyl; and when R$_1$=ethyl; R$_2$=ethyl; R$_3$ is selected from hydrogen, straight or branched (C$_1$-C$_3$)alkyl group such as methyl, ethyl, n-propyl or 1-methylethyl; (C$_6$-C$_{10}$)aryl group such as phenyl, α-naphthyl or β-naphthyl; (C$_7$-C$_9$)aralkyl group such as benzyl, 1-phenylethyl, 2-phenylethyl or phenylpropyl; a heterocycle group such as 2 or 3-furanyl, 2 or 3-thienyl, 2,3 or 4-pyridyl, di(C$_1$-C$_3$)alkyl substituted pyridyl, benzofuranyl, benzothienyl, quinolinyl or —(CH$_2$)$_n$COOR$_5$ when n=1-4 and R$_5$ is selected from hydrogen; straight or branched (C$_1$C$_3$)alkyl group such as methyl, ethyl, n-propyl or 1-methylethyl; or (C$_6$-C$_{10}$) aryl group such as phenyl, α-naphthyl, β-naphthyl; R$_4$ is selected from hydrogen; straight or branched (C$_1$-C$_3$)alkyl group such as methyl, ethyl, n-propyl or 1-methylethyl; (C$_6$-C$_{10}$)aryl group such as phenyl, α-naphthyl or β-naphthyl; (C$_7$-C$_9$)aralkyl group such as benzyl, 1-phenylethyl, 2-phenylethyl or phenylpropyl; a heterocycle group such as 2 or 3-furanyl, 2 or 3-thienyl, 2,3 or 4-pyridyl, di($C_1$-$C_3$)alkyl substituted pyridyl, benzofuranyl, benzothienyl, quinolinyl or —$(CH_2)_n COOR_6$ when n=1-4 and $R_6$ is selected from hydrogen; straight or branched ($C_1$-$C_3$)alkyl such as methyl, ethyl, n-propyl or 1-methylethyl; or ($C_6$-$C_{10}$)aryl such as phenyl, α-naphthyl or β-naphthyl; or $R_3$ and $R_4$ taken together are —$(CH_{22}W(CH_2)$—, wherein W is selected from $(CH_2)_n$ and n=0-1, —NH, —N($C_1$-$C_3$)— alkyl, —N($C_1$-$C_4$)alkoxy, oxygen, sulfur or substituted congeners selected from (L or D) proline, ethyl (L or D) prolinate, morpholine, pyrrolidine or piperidine; and the pharmacologically acceptable organic and inorganic salts, and metal complexes.

DESCRIPTION OF THE PREFERRED EMBODIMENTS

The novel compounds of the present invention may be readily prepared in accordance with the following schemes.

The starting 7-(substituted amino)-6-demethyl-6-deoxytetracyclines described in formula 1, wherein R=$NR_1R_2$ and $R_1$=$R_2$ (1a) and R=$NHR_2$ (1b) or the salts thereof are prepared by procedures known to those skilled in the art including those described in U.S. Pat. Nos. 3,226,436 and 3,518,306.

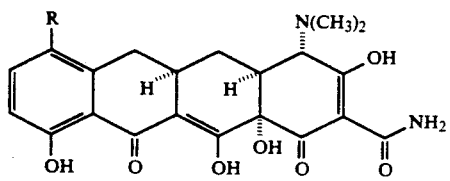

1a = R = $NR_1R_2$, $R_1$ = $R_2$
1b = R = $NHR_2$
1c = R = $NR_1R_2$, $R_1 \neq R_2$ The starting 7-(substituted amino)-6-demethyl-6-deoxytetracyclines described in formula 1 wherein R=$NR_1R_2$ and $R_1 \neq R_2$ (1c) are prepared according to Scheme 1.

Scheme I

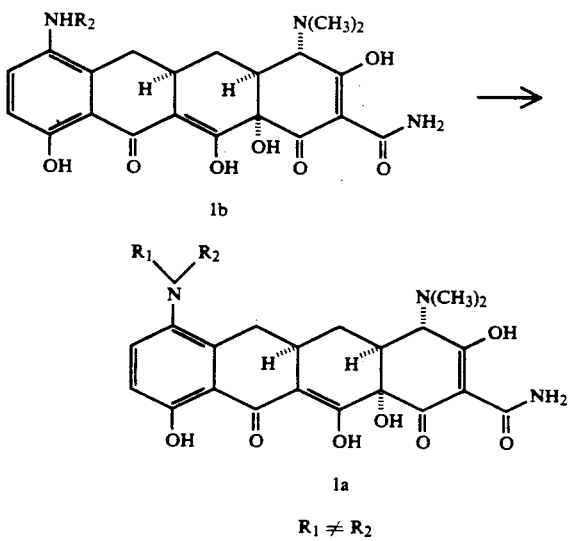

$R_1 \neq R_2$

In accordance with Scheme I, a 7-(monoalkylamino)-6-demethyl-6-deoxytetracycline, 1b, in which R=$NHR_2$, is reductively alkylated with an aldehyde to give an unsymmetrical dialkylamino, 1c.

Scheme II

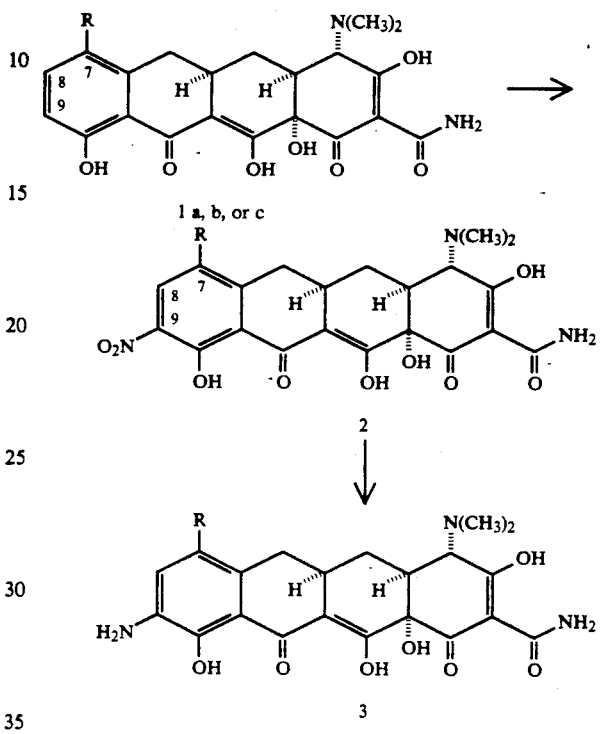

In accordance with Scheme II, a 7-(substituted amino)-6-demethyl-6-deoxytetracycline or its salts, 1a–1c, is treated with a) a metal nitrate salt; such as calcium, potassium or sodium; and a strong acid; such as sulfuric acid, trifluoroacetic acid, methanesulfonic acid or perchloric acid or b) nitric acid and a strong acid; such as sulfuric acid, trifluoroacetic acid, methanesulfonic acid or perchloric acid; to form the corresponding 7-(substituted amino)-9-nitro-6-demethyl-6-deoxytetracycline 2.

To produce the 9-(amino)-7-(substituted amino)-6-demethyl-6-deoxytetracyclines of the present invention, compound 2 or its salts is treated with hydrogen in an acid alcohol solvent, preferably 2-methoxyethanol, in the presence of a suitable catalyst such as, for example:
a) any supported catalyst; such as 0.5-25% palladium-on-carbon, 0.5-25%- palladium-on-barium sulfate, 0.5-25% platinum-on-carbon or 0.5-25% rhodium-on-carbon;

b) any reducible metal oxide catalyst; such as Raney nickel or platinum oxide; or c) a homogeneous hydrogenation catalyst; such as tris(triphenylphosphine)rhodium (I) chloride; to obtain the 9-amino-7-(substituted amino)-6-demethyl-6-deoxytetracycline, 3.

Alternatively, the 9-(amino)-7-(substituted amino)-6-demethyl-6-deoxytetracyclines of the present invention are obtained by treating with:

a) stannous chloride dihydrate as described by R. B. Wordward, Org. Syn., Coll. Vol. 3, 453 (1955);

b) a soluble metal sulfide, preferably sodium sulfide, in alcoholic solvents as described by G. R. Robertson, Org. Syn., Coll. Vol. 1, 52 (1941);

c) an active metal in mineral acid; such as iron, tin or zinc in dilute hydrochloric acid;

d) active metal couples; such as copper-zinc, tin-mercury or aluminum amalgam in dilute acid; or e) transfer hydrogenation using triethylammonium formate and a supported catalyst as described by I. D. Entwistle et al., J. Chem. Soc., Perkin 1, 443 (1977).

Scheme III

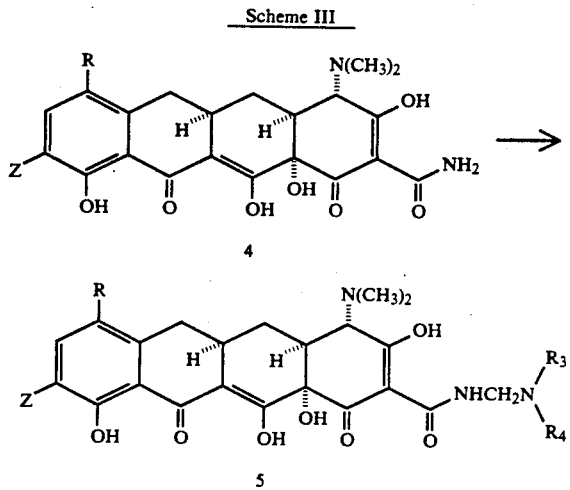

In accordance with Scheme III, $Z=NO_2$ or $NH_2$; compound 4 is selectively N-alkylated in the presence of formaldehyde and either a primary amine such as methylamine, ethylamine, benzylamine, methyl glycinate, (L or D) lysine, (L or D) alanine or their substituted congeners; or a secondary amine such as morpholine, pyrrolidine, piperidine or their substituted congeners to give the corresponding Mannich base adducts, 5, of the biologically active 7-(substituted amino)-6-demethyl-6-deoxytetracyclines. Contemplated equivalents include those substituted morpholine, pyrrolidine or piperidine moieties wherein the substituents are chosen to provide the requisite increase in solubility without adversely affecting antibacterial activity.

The 9-amino-7-(substituted amino)-6-demethyl-6-deoxytetracyclines, 3, may also be obtained as metal complexes such as aluminum, calcium, iron, magnesium, manganese and complex salts; inorganic and organic salts and corresponding Mannich base adducts using methods known to those skilled in the art. Preferably, the 9-amino-7-(substituted amino)-6-demethyl-6-deoxytetracyclines, are obtained as inorganic salts such as hydrochloric, hydrobromic, hydroiodic, phosphoric, nitric or sulfate; or organic salts such as acetate, benzoate, citrate, cysteine or other amino acids, fumarate, glycolate, maleate, succinate, tartrate, alkylsulfonate or arylsulfonate. In all cases, the salt formation occurs With the C(4)-dimethylamino group. The salts are preferred for oral and parenteral administration.

Biological Activity

Methods for In Vitro Antibacterial Evaluation (Table 1)

The minimum inhibitory concentration (MIC), the lowest concentration of the antibiotic which inhibits growth of the test organism, is determined by the microtiter broth dilution method using 0.1 ml Muller-Hinton II broth (Baltimore Biological Laboratories) per well. A suitable oxygen scavenger (i.e., cysteine or dithiothreitol) is added to the assay medium for the testing of compounds according to Formula I because of the sensitivity of those compounds to oxidation. An inoculum level of $1-5 \times 10^5$ CFU/ml and a range of antibiotic concentrations (32 0.004 μg/ml) are used. MIC's were determined after the plates were incubated for 18 hours at 35° C. in a forced air incubator.

E. coli in vitro protein translation system (Table 2)

The E. coli in vitro translation system can be used to study not only the mechanism of protein translation itself, but also the effect that various compounds may have on protein synthesis. The system can be set up to function as a coupled transcription and translation system or as a translation only system depending on whether DNA or RNA is added to initiate protein synthesis. In this way, compounds affecting either RNA synthesis and/or protein synthesis can be studied. Protein synthesis is monitored by the incorporation of radiolabeled amino acids into trichloroacetic acid precipitable material. The system used is based upon literature methods [G. Zubay, Ann. Rev. Genet., 7: 267–287(1973) and J. Collins, Gene, 6: 28–42 (1979)].

The system used to study tetracycline protein synthesis inhibition is as follows:

An S30 extract (supernatant from a $30,000 \times G$ centrifugation of lysed cells) of either tetracycline sensitive or tetracycline resistant (tetM+) cells is combined with a mixture of low molecular weight compounds required for protein synthesis which include a mixture of 19 amino acids, methionine, $^{35}$S-methionine, plasmid template DNA and either dimethylsulfoxide (DMSO) or the tetracycline to be tested dissolved and diluted in DMSO. This mixture is incubated at 37° C. for 30 minutes. Following the incubation, 2.5 μl of the 10 μl reaction is removed and added to 0.5 ml of 1N sodium hydroxide. The solution is incubated an additional 15 minutes at 37° C., to destroy any m-RNA and t-RNA. The incorporation of $^{35}$S-methionine is determined by precipitating the high molecular weight material in the sodium hydroxide aliquot with trichloroacetic acid (TCA), collecting the precipitated material on Whatman G/FC filters, drying the filters and counting the radioactivity retained on the filter. Percent inhibition (P.I.) of protein synthesis is determined by the following equation:

$$P.I. = 100 - \left( \frac{\text{total } CPM^* \text{ retained on filter in the presence of added tetracycline compound}}{\text{Total } CPM^* \text{ retained on filter for DMSO (control)}} \right) \times 100$$

*CPM = counts per minute

In Vivo Antibacterial Evaluation (Table 3)

The therapeutic effects of tetracyclines are determined against acute lethal infections with various staphylococcal and E. coli strains. Female mice, strain CD-1 Charles River Laboratories, (20±2 grams) are challenged by an intraperitoneal injection of sufficient bacteria (suspended in broth or hog gastric mucin) to kill non-treated controls within 24–48 hours. Antibacterial agents, contained in 0.5 ml of 0.2% aqueous agar, are administered subcutaneously or orally 30 minutes after infection. When an oral dosing schedule is used, animals are deprived of food for 5 hours before and 2 hours after infection. Five mice are treated at each dose level. The 7 day survival ratios from three separate tests are pooled for calculation of median effective dose (ED$_{50}$).

Legend for Tables I–III

A = 9-Amino-7-(dimethylamino)-6-demethyl-6-deoxytetracycline hydrochloride

B = 7-(Dimethylamino)-6-demethyl-6-deoxytetracycline hydrochloride (minocycline hydrochloride)

C = 9-Amino-7-(diethylamino)-6-demethyl-6-deoxytetracycline sulfate

D = 7-(Diethylamino)-6-demethyl-6-deoxytetracycline sulfate

TABLE 1

In Vitro Antibacterial Activity of
6-Demethyl-6-deoxytetracycline Derivatives

| Organism* | MIC (ug/ml) | | | |
|---|---|---|---|---|
| | A$^a$ | B | C$^a$ | D |
| S. aureus UBMS 88-5 (tetM) | 0.06 | 4 | 0.5 | 16 |
| S. aureus UBMS 88-4 (tetracycline-sensitive) | 0.015 | 0.008 | 0.03 | 0.03 |
| S. aureus UBMS 90-1 (tetM) | 0.25 | 4 | 2 | 8 |
| S. aureus UBMS 90-2 (tetM) | 0.06 | 1 | 0.25 | 8 |
| S. aureus UBMS 90-3 (tetracycline-sensitive) | 0.015 | 0.015 | 0.03 | 0.03 |
| S. aureus UBMS 88-7 (tetK) | 0.12 | 0.03 | 0.06 | 0.12 |
| S. aureus IVES 2943 (methicillin-resistant) | 0.5 | 1 | 0.25 | 8 |
| S. aureus IVES 1983 (methicillin-resistant) | 0.5 | 1 | 0.25 | 8 |
| S. aureus CI 2371 (methicillin-resistant) | 0.5 | 4 | NA | NA |
| S. aureus CI 3300 (methicillin-resistant) | 0.25 | 8 | NA | NA |
| Coagulase negative staphylococci CI 664 | 0.003 | 0.015 | NA | NA |
| Coagulase negative staphylococci CI 535 | 1 | 8 | NA | NA |
| S. haemolyticus AVAH 88-3 | 0.06 | 0.12 | 0.12 | NA |
| E. faecalis AMV 120 (tetM) | 4 | 16 | NA | NA |
| E. faecalis PAM 211 (tetN) | 4 | 16 | NA | NA |
| E. faecalis 12201 (vancomycin-resistant) | 0.5 | 4 | NA | NA |
| E. faecalis CI 2735 | 0.5 | 4 | NA | NA |
| E. coli UBMS 88-1 (tetB) | >32 | 8 | 2 | 32 |
| E. coli UBMS 88-2 (tetracycline-sensitive) | 0.25 | 0.5 | 0.5 | 2 |
| E. coli UBMS 89-1 (tetM) | 1 | 8 | 2 | NA |
| E. coli UBMS 89-2 (tetracycline-sensitive) | 0.5 | 0.5 | 0.5 | 4 |
| E. coli UBMS 90-4 (tetM) | 4 | >32 | 32 | >32 |
| E. coli UBMS 90-5 (tetracycline-sensitive) | 0.25 | 0.5 | 1 | 2 |
| M. morganii NEMC 87-119 | 2 | 2 | 2 | 32 |
| S. marcescens FPOR 87-33 | 4 | 2 | 4 | 32 |
| P. aeruginosa ATCC 27853 | 2 | 4 | 8 | 32 |
| X. maltophilia FPOR 87-210 | 0.12 | 0.06 | 0.12 | 0.25 |
| E. coli ATCC 25922 | 0.25 | 0.25 | 0.50 | 1 |
| E. faecalis ATCC 29212 | 0.06 | 0.25 | 0.12 | 8 |
| S. aureus ATCC 29213 | 0.008 | ≦0.004 | ≦0.015 | <0.015 |

$^a$In vitro assay is done in the presence of cysteine (0.05%). Antibacterial potency of B and D was not enhanced in the presence of cysteine.

*The tetM resistance determinant protects ribosomes from tetracycline, the tetK determinant promotes efflux of the drug from the cell.

TABLE 2

In Vitro Protein Translation with E. coli S30 Ribosomes

| | Wild Type Version | | | | | | | |
|---|---|---|---|---|---|---|---|---|
| | B | | | | A | | | |
| | Wild Type S30 no DTT* | | Wild Type S30 with DTT* | | Wild Type S30 no DTT* | | Wild Type S30 with DTT | |
| Reaction | Counts | % Inhibition | Counts | % Inhibition | Counts | % Inhibition | Counts | % Inhibition |
| Control DMSO Plus compound | 457268 | | 872132 | | 457268 | | 872132 | |
| 1.0 mg/ml | 57696 | 87 | 58885 | 93 | 52595 | 88 | 38121 | 96 |
| 1:2 Dilution | 76804 | 83 | 78961 | 91 | 80494 | 82 | 60891 | 93 |
| 1:4 Dilution | 53400 | 88 | 111971 | 87 | 95015 | 79 | 92203 | 89 |
| 1:8 Dilution | 162405 | 64 | 149792 | 83 | 130209 | 72 | 143215 | 84 |
| 1:16 Dilution | 213077 | 53 | 207484 | 76 | 205392 | 55 | 214831 | 75 |
| 1:32 Dilution | 306650 | 33 | 289304 | 67 | 297786 | 35 | 238321 | 73 |
| 1:64 Dilution | 457601 | 0 | 518601 | 41 | 245494 | 46 | 380103 | 56 |

| | tetM Variant | | | | | | | |
|---|---|---|---|---|---|---|---|---|
| | tetM S30 no DTT* | | tetM S30 with DTT* | | tetM S30 no DTT* | | tetM S30 with DTT* | |
| Reaction | Counts | % Inhibition | Counts | % Inhibition | Counts | % Inhibition | Counts | % Inhibition |
| Control DMSO Plus compound | 247938 | | 447247 | | 247938 | | 447247 | |
| 1.0 mg/ml | 281528 | 0 | 371475 | 17 | 129780 | 48 | 145068 | 68 |
| 1:2 Dilution | 258633 | 0 | 331439 | 26 | 158861 | 36 | 168574 | 62 |
| 1:4 Dilution | 248904 | 0 | 373168 | 17 | 203184 | 18 | 226708 | 49 |
| 1:8 Dilution | 289595 | 0 | 421533 | 6 | 231447 | 7 | 284606 | 36 |
| 1:16 Dilution | 287498 | 0 | 493679 | 0 | 305633 | 0 | 375989 | 16 |
| 1:32 Dilution | 262329 | 0 | 490283 | 0 | 349994 | 0 | 412967 | 8 |
| 1:64 Dilution | 249242 | 0 | 452837 | 0 | 310723 | 0 | 507461 | 0 |

*Dithiothreitol (DTT) is used as an exygen scavenger.

TABLE 3

Effects of Compounds A and B on Acute Lethal Infections in Mice

| Organism | Route of Antibiotic Administration* | ED$_{50}$ (mg/kg)+ A | B |
| --- | --- | --- | --- |
| E. coli 311 (sens) | Subcutaneous | 2.8 | 3.1 |
| E. coli UBMS 90-4 (tetM) | Subcutaneous | 24 | >256 |
| S. aureus UBMS 90-1 (tetM) | Subcutaneous | 0.30 | 1.7 |
| S. aureus UBMS 90-2 (tetM) | Oral | 1.6 | 1.8 |
| | Subcutaneous | 0.53 | 1.8 |
| S. aureus Smith (sens) | Oral | 0.81 | 0.53 |
| | Subcutaneous | 0.34 | 0.32 |

*Single Dose
+Median effective dose protecting 50% of the infected mice

Testing Results

As seen from the above testing, the compounds according to the present invention display good activity against a spectrum of tetracycline sensitive and resistant Gram-positive and Gram-negative bacteria, especially strains of E. coli, S. aureus and E. faecalis containing the tetM or tetK resistant determinants. As illustrated in Table I, 9-amino-7-(dimethylamino)-6-demethyl-6-deoxytetracycline hydrochloride (A) shows good in vitro activity against tetracycline resistant strains carrying the tetM resistance determinant such as S. aureus UBMS 88-5, S. aureus UBMS 90-1 and 90-2, E. coli UBMS 89-1 and 90-4; and is equally as effective as 7-(dimethylamino)-6-demethyl-6-deoxytetracycline hydrochloride (B) vs. susceptible strains. 7-(dimethylamino)-6-demethyl-6-deoxytetracycline hydrochloride (B) and 9-amino-7-(dimethylamino)-6-demethyl-6-deoxytetracycline hydrochloride (A) are assayed in vitro for their ability to inhibit protein synthesis, taking place on either wild type or tetM protected ribosomes, using a coupled transcription and translation system. Similarly, 9-amino-7-(diethylamino)-6-demethyl-6-deoxytetracycline sulfate (C) shows enhancement of antibacterial activity versus 7-(diethylamino)-6-demethyl-6-deoxytetracycline sulfate (D).

Both compounds (A & B) are found to effectively inhibit protein synthesis on wild type ribosomes, having equivalent levels of activity (Table II). 7-(dimethylamino)-6-demethyl-6-deoxytetracycline hydrochloride (B) is unable to inhibit protein synthesis occurring on tetM protected ribosomes. In contrast, 9-amino-7-(dimethylamino)-6-demethyl-6-deoxytetracycline hydrochloride (A) is effective in inhibiting protein synthesis occurring on tetM protected ribosomes, although higher drug levels are required to achieve similar levels of inhibition relative to wild type ribosomes.

The enhanced activity of 9-amino-7-(dimethylamino)-6-demethyl-6-deoxytetracycline sulfate (A) against tetracycline susceptible and resistant organisms (tetM) is demonstrated in Table 3 for animals infected with representative bacteria. Lowered ED$_{50}$'s are obtained with 9-amino-7-(dimethylamino)-6-demethyl-6-deoxytetracycline sulfate (A) than with 7-(dimethylamino)-6-demethyl-6-deoxytetracycline hydrochloride (B) in mice with of S. aureus and E. coli which carry the tetM resistance determinant. Similar ED$_{50}$'s are obtained with 9-amino-7-(dimethylamino)-6-demethyl-6-deoxytetracycline sulfate (A) and 7-(dimethylamino)-6-demethyl-6-deoxytetracycline hydrochloride (B) against infections with minocycline susceptible organisms.

As can be seen from Tables 1 and 3, the new 9-amino-7-(substituted amino)-6-demethyl-6-deoxytetracyclines may be used to prevent or control important veterinary diseases such as mastitis, diarrhea, urinary tract infections, skin infections, ear infections, wound infections and the like.

The improved efficacy of the new 9-amino-7-(substituted amino)-6-demethyl-6-deoxytetracyclines is evidenced by the in vitro activity against isogenic strains into which the resistant determinants, such as tetM were cloned (Table 1); the inhibition of protein synthesis by tetM resistant ribosomes (Table 2); and the in vivo activity against experimental infections caused by strains resistant to the tetracyclines, due to the presence of resistant determinants, tetM (Table 3).

When the compounds are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 2.0 mg/kg of body weight to 100.0 mg/kg of body weight should be administered one to four times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention will be more fully described in conjunction with the following specific examples which are not to be construed as limiting the scope of the invention.

EXAMPLE 1

[4S-(4α,12aα)]-4,7-Bis(dimethylamino)-1,4,4a,5,5a,6,11,12a-octahydro-3,10,12,12a-tetrahydroxy-9-nitro-1,11-dioxo-2-naphthacenecarboxamide sulfate (1:1)

To a stirred ice bath cooled solution of 0.444 g of [4S-(4α,12aα)]-4,7-bis(dimethylamino)-1,4,4a,5,5a,6,11,-12a-octahydro-3,10,12,12a-tetrahydroxy-1,11-dioxo-2-naphthacenecarboxamide hydrochloride, prepared by the procedure described in U.S. Pat. No. 3,226,436, dissolved in 15 ml of sulfuric acid is added 0.101 g of sodium nitrate. The mixture is stirred in the cold for 45 minutes followed by the dropwise addition to 500 ml of diethyl ether. The resulting solid is collected, washed with diethyl ether and dried to give 0.6 g of the desired product as a solid. MS(FAB): m/z 503(M+H) and 601(M+H$_2$SO$_4$+H).

EXAMPLE 2

[4S-(4α,12aα)]-7-(Diethylamino)-4-(dimethylamino)-1,4,4a,5,5a,6,11,12a-octahydro-3,10,12,12a-tetrahydroxy-9-nitro-1,11-dioxo-2-naphthacenecarboxamide sulfate (1:2)

To a stirred ice cooled solution of 0.660 g of [4S-(4α,12aα)]-7-(diethylamino)-4-(dimethylamino)-1,4,4a,5,5a,6,11,12a-octahydro-3,10,12,12a-tetrahydroxy-1,11-dioxo-2-naphthacenecarboxamide hydrochloride, prepared by the procedure described in U.S. Pat. No. 3,226,436, dissolved in 15 ml of sulfuric acid is added 0.151 g of sodium nitrate. The mixture is stirred in the cold followed by dropwise addition to 500 ml of diethyl ether. The resulting solid is collected, washed with diethyl ether and dried to give 0.8 g of the desired product as a solid. MS(FAB): m/z 531(M+H) and 629(M+H$_2$SO$_4$+H).

EXAMPLE 3

[4S-(4α,12aα)]-9-Amino-4,7-bis(dimethylamino)-1,4,4a,5,5a,6,11,12a-octahydro-3,10,12,12a-tetrahydroxy-1,11-dioxo-2-naphthacenecarboxamide sulfate (1:1)

A mixture of 2.0 g of product from Example 1 in 20 ml of 2-methoxyethanol is stirred for 10 minutes and filtered. The filtrate is shaken, in a pressure bottle, with 1.0 g of 10% palladium-on-carbon and 5 ml of 2N sulfuric acid, under 30 lbs. of hydrogen pressure, for 1 hour. The reaction mixture is filtered and the filtrate concentrated in vacuo to half volume. The solution is poured into 100 ml of diethyl ether, the solid collected, washed with diethyl ether and dried to give 1.6 g of the desired product as a solid. MS(FAB): m/z 473(M+H).

EXAMPLE 4

[4S-(4α,12α)]-Amino-4,7-bis(dimethylamino)-1,4,4a,5,5a,6,11,12a-octahydro-3,10,12,12a-tetrahydroxy-1,11-dioxo-2-naphthacenecarboxamide hydrochloride (1:1)

A mixture of 20.0 g of product from Example 1 in 250 ml of 2-methoxyethanol is stirred for 10 minutes and filtered. The filtrate is shaken, in a pressure bottle, with 10.0 g of 10% palladium-on-carbon and 100 ml of 1N ethanolic hydrogen chloride, under 30 lbs. of hydrogen pressure, for 1 hour. The reaction mixture is filtered and the filtrate concentrated in vacuo to half volume. The solution is poured into 1 L of diethyl ether, the solid collected, washed with diethyl ether and dried to give 16.0 g of the desired product as an oil. The oil is suspended in 20 ml of distilled water, made acidic with 2.8 ml of 32% hydrochloric acid and decolorized with charcoal. The mixture is filtered through diatomaceous earth and made basic (pH 4.0) with concentrated ammonium hydroxide. The solid is collected at 4° C., washed with pH 4 water and dried in vacuo to give 14.2 g of the desired product as a solid.

$^1$H NMR (CD$_3$SOCD$_3$): δ 4.19(s,1H,4-H) and 7.29(s,1H,8-H). MS(FAB): m/z 473(M+H).

Analysis for C$_{23}$H$_{28}$ N$_4$O$_7$ HCl 6.7% H$_2$O. Calc'd: C,50.64; H,6.10; N,10.27; Cl,6.50. Found: C,50.72; H,6.07; N,10.27; Cl,6.62.

EXAMPLE 5

[4S-(4α12α)]-Amino-4,7-bis(dimethylamino)-1,4,4a,5,5a,6,11,12a-octahydro-3,10,12,12a-tetrahydroxy-1,11-dioxo-2-naphthacenecarboxamide p-toluenesulfonate (1:1)

The title compound is prepared by the procedure of Example 4, using 20 g of product from Example 1, to give 16.0 g of the desired product as the free base. The free base is suspended in 20 ml of distilled water, made acidic with p-toluenesulfonic acid monohydrate and decolorized with charcoal. The mixture is filtered through diatomaceous earth and made basic (pH 4.0) with concentrated ammonium hydroxide. The solid is collected at 4° C., washed with pH 4 water and dried in vacuo to give 16.0 g of the desired product.

EXAMPLE 6

[4S-(4α,12α)]-Amino-7-(diethylamino)-4-(dimethylamino)-1,4,4a,5,5a,6,11,12a-octahydro-3,10,12 12a-tetrahydroxy-1,11-dioxo-2-naphthacenecarboxamide sulfate (1:2)

The title compound is prepared by the procedure of Example 3, using 2.1 g of product from Example 2, to give 1.5 g of the desired product as a solid. $^1$H NMR (CD$_3$SOCD$_3$) δ 4.25(s,1H,4-H) and 7.27(s,1H,8-H). MS(FAB): m/z 501(M+H) and 599(M+H$_2$SO$_4$+H).

EXAMPLE 7

[4S-(4α,12aα)]4-(Dimethylamino)-7-(ethylmethylamino)-1,4,4a,5,5a,6,11,12a-octahydro-3,10,12,12a-tetrahydroxy-1,11-dioxo-2-naphthacenecarboxamide hydrochloride (1:1)

A solution of 0.460 g of [4S-(4α,12aα)]-4-(dimethylamino]-7-(ethylamino)-1,4,4a,5,5a,6,11,12a-octahydro-3,10,12,12a-tetrahydroxy-1,11-dioxo-2-naphthacenecarboxamide hydrochloride, prepared by the procedure described in U.S. Pat. No. 3,226,436, 0.5 ml of 97% formic acid and 0.75 ml of 40% aqueous formaldehyde is heated at reflux temperature for 2 hours. The reaction mixture is cooled, concentrated in vacuo to half volume and poured into diethyl ether. The resulting solid is collected, washed with diethyl ether and dried to give 0.3 g of the desired product as a solid.

EXAMPLE 8

[4S-(4α,12aα)]-4-(Dimethylamino)-7-(ethylmethylamino)-1,4,4a,5,5a,6,11,12a-octahydro-3,10,12,12a-tetrahydro-9-nitro-1,11-dioxo-2-naphthacenecarboxamide sulfate (1:1)

The title compound is prepared by the procedure of Example 1, using 0.46 g of product from Example 7 to give 0.5 g of the desired product as a solid.

EXAMPLE 9

[4S-(4α,12aα)]-Amino-4-(dimethylamino)-7-(ethylmethylamino)-1,4,4a,5a,6,11,12a-octahydro-3,10,12,12a-tetrahydroxy-1,11-dioxo-2-naphthacenecarboxamide sulfate (1:1)

The title compound is prepared by the procedure of Example 3, using 1.0 g of product from Example 8, to give 0.8 g of the desired product as a solid.

EXAMPLE 10

[4S-(4α,12aα)]-4-(Dimethylamino)-7-[(1-methylethyl)amino]-1,4,4a,5,5a,6,11,12a-octahydro-3,10,12,12a-tetrahydroxy-9-nitro-1,11-dioxo-2-naphthacenecarboxamide sulfate (1:1)

The title compound is prepared by the procedure of Example 1, using 0.48 g of [4S-(4α,12aα)]-4-(dimethylamino)-7-[(1-methylethyl)amino]-1,4,4a,5,5a,-6,11,12a-octahydro-3,10,12,12a-tetrahydroxy-1,11-dioxo-2-naphthacenecarboxamide hydrochloride, prepared by the procedure described in U.S. Pat. No. 3,226,436, to give 0.5 g of the desired product as a solid.

EXAMPLE 11

[4S-(4α,12aα)]-Amino-4-(dimethylamino)-7-[(1-methylethyl)amino]-1,4,4a,5,5a,6,11,12a-octahydro3,10,12,12a-tetrahydroxy-1,11-dioxo-2-naphthacenecarboxamide sulfate (1:1)

The title compound is prepared by the procedure of Example 3, using 2.1 g of product from Example 10, to give 1.5 g of the desired product as a solid.

EXAMPLE 12

[4S-(4α12aα)]-4-(Dimethylamino)-7-(ethylamino)-1,4,4a,5,5a,6,11,12a-octahydro-3,10,12,12a-tetrahydroxy-9-nitro-1,11-dioxo-2-naphthacenecarboxamide sulfate (1:1)

The title compound is prepared by the procedure of Example 1, using 0.96 g of [4S-(4α,12aα)]-4-(dimethylamino)-7-(ethylamino)-1,4,4a,5,5a,6,11,12a-octahydro-3,10,12,12a-tetrahydroxy-1,11-dioxo-2-naphthacenecarboxamide prepared by the procedure described in U.S. Pat. No. 3,226,436, to give 0.9 g of the desired product as a solid.

EXAMPLE 13

[4S-(4α,12aα)]-Amino-4-(dimethylamino)-7-(ethylamino)-1,4,4a,5,5a,6,11,12a-octahydro-3,10,12,12a-tetrahydroxy-1,11-dioxo-2-naphthacenecarboxamide sulfate (1:1)

The title compound is prepared by the procedure of Example 3, using 1.0 g of product from Example 12, to give 0.7 g of the desired product as a solid.

EXAMPLES 14-35

Substantially following the methods described in detail hereinabove in Examples 3 and 9, the compounds of this invention listed below in Examples 14-35 are prepared.

EXAMPLE 14

[4S-(4α,12aα)]-9-Amino-4-(dimethylamino)-7-(methylpropylamino)-1,4,4a,5,5a,6,11,12a-octahydro-3,10,12,12a-tetrahydroxy-1,11-dioxo-2-naphthacenecarboxamide sulfate.

EXAMPLE 15

[4S-(4α,12aα)]-9-Amino-4-(dimethylamino)-7-(butylmethylamino)-1,4,4a,5,5a,6,11,12a-octahydro-3,10,12,12a-tetrahydroxy-1,11-dioxo-2-naphthacenecarboxamide sulfate.

EXAMPLE 16

4S-(4α,12aα)]-9-Amino-4-(dimethylamino)-7-[1-methylpropylamino)methylamino]-1,4,4a,5,5a,6,11,12a-octahydro-3,10,12,12a-tetrahydroxy-1,11-dioxo-2-naphthacenecarboxamide sulfate.

EXAMPLE 17

[4S-(4α,12aα)]-9-Amino-4-(dimethylamino)-7-[(2-methylpropyl)methylamino]-1,4,4a,5,5a,6,11,12a-octahydro-3,10,12,12a-tetrahydroxy-1,11-dioxo-2-naphthacenecarboxamide sulfate.

EXAMPLE 18

[4S-(4α,12aα) )]-9-Amino-4-(dimethylamino)-7-(ethylpropylamino)-1,4,4a,5,5a,6,11,12a-octahydro-3,10,12,12a-tetrahydroxy-1,11-dioxo-2-naphthacenecarboxamide sulfate.

EXAMPLE 19

[4S-(4α,12aα))]-9-Amino-4-(dimethylamino)-7-[(1-methylethyl)ethylamino)-1,4,4a,5,5a,6,11,12a-octahydro-3,10,12,12a-tetrahydroxy-1,11-dioxo-2-naphthacenecarboxamide sulfate.

EXAMPLE 20

[4S-(4α,12aα) )]-9-Amino-4-(dimethylamino)-7-(butylethylamino)-1,4,4a,5,5a,6,11,12a-octahydro-3,10,12,12a-tetrahydroxy-1,11-dioxo-2-naphthacenecarboxamide sulfate.

EXAMPLE 21

[4S-(4α,12aα))]-9-Amino-4-(dimethylamino)-7-[(1-methylpropyl)ethylamino]-1,4,4a,5,5a,6,11,12a-octahydro-3,10,12,12a-tetrahydroxy-1,11-dioxo-2-naphthacenecarboxamide sulfate.

EXAMPLE 22

[4S-(4α,12aα))]-9-Amino-4-(dimethylamino)-7-[(2-methylpropyl)ethylamino]-1,4,4a,5,5a,6,11,12a-octahydro-3,10,12,12a-tetrahydroxy-1,11-dioxo-2-naphthacenecarboxamide sulfate.

EXAMPLE 23

[4S-(4α,12aα)]-9-Amino-4-(dimethylamino)-7-(dipropyl-amino)-1,4,4a,5,5a,6,11,12a-octahydro-3,10,12,12a-tetrahydroxy-1,11-dioxo-2-naphthacenecarboxamide sulfate.

EXAMPLE 24

[4S-(4α,12aα)]-9-Amino-4-(dimethylamino)-7-[(1-methyethyl)propylamino]-1,4,4a,5,5a,6,11,12a-octahydro-3,10,12,12a-tetrahydroxy-1,11-dioxo-2-naphthacenecarboxamide sulfate.

EXAMPLE 25

[4S-(4α,12aα) ]-9-Amino-4-(dimethylamino)-7-(butylpropylamino)-1,4,4a,5,5a,6,11,12a-octahydro-3,10,12,12a-tetrahydroxy-1,11-dioxo-2-naphthacenecarboxamide sulfate.

EXAMPLE 26

[4S-(4α,12aα)]-9-Amino-4-(dimethylamino)-7-[(1-methylpropyl)propylamino]-1,4,4a,5,5a,6,11,12a-octahydro-3,10,12,12a-tetrahydroxy-1,11-dioxo-2-naphthacenecarboxamide sulfate.

EXAMPLE 27

[4S-(4α,12aα)]-9-Amino-4-(dimethylamino)-7-[(2-methylpropyl)propylamino]-1,4,4a,5,5a,6,11,12a-octahydro-3,10,12,12a-tetrahydroxy-1,11-dioxo-2-naphthacenecarboxamide sulfate.

EXAMPLE 28

[4S-(4α,12aα)]-9-Amino-4-(dimethylamino)-7-[(1-methylethyl)butylamino]-1,4,4a,5,5a,6,11,12a-octahydro-3,10,12,12a-tetrahydroxy-1,11-dioxo-2-naphthacenecarboxamide sulfate.

EXAMPLE 29

[4S-(4α,12aα)]-9-Amino-4-(dimethylamino)-7-[(1-methylethyl)(1-methylpropyl)amino]-1,4,4a,5,5a,6,11,-12a-octahydro-3,10,12,12a-tetrahydroxy-1,11-dioxo-2-naphthacenecarboxamide sulfate.

EXAMPLE 30

[4S-(4α,12aα)]-9-Amino-4-(dimethylamino)-7-[(1-methylethyl)(2-methylpropyl)amino]-1,4,4a,5,5a,6,11,-12a-octahydro-3,10,12,12a-tetrahydroxy-1,11-dioxo-2-naphthacenecarboxamide sulfate.

EXAMPLE 31

[4S-(4α,12aα)]-9-Amino-4-(dimethylamino)-7-(dibutylamino)-1,4,4a,5,5a,6,11,12a-octahydro-3,10,12,12a-tetrahydroxy-1,11-dioxo-2-naphthacenecarboxamide sulfate.

EXAMPLE 32

[4S-(4α,12aα)]-9-Amino-4-(dimethylamino)-7-[(1-methyl-3,10,12,12a-tetrahydroxy-1,11-dioxo-2-naphthacenecarboxamide sulfate.

EXAMPLE 33

[4S-(4α,12aα)]-9-Amino-4-(dimethylamino)-7-[(2-methylpropyl)butylamino]-1,4,4a,5,5a,6,11,12a-octahydro-3,10,12,12a-tetrahydroxy-1,11-dioxo-2-naphthacenecarboxamide sulfate.

EXAMPLE 34

[4S-(4α,12aα)]-9-Amino-4-(dimethylamino)-7-[(1-methylpropyl)amino]-1,4,4a,5,5a,6,11,12a-octahydro-3,10,12,12a-tetrahydroxy-1,11-dioxo-2-naphthacenecarboxamide sulfate.

EXAMPLE 35

[4S-(4α,12aα)]-9-Amino-4-(dimethylamino)-7-[(1-methylpropyl)(2-methylpropyl)amino]-1,4,4a,5-,5a,6,11,12a-octahydro-3,10,12,12a-tetrahydroxy-1,11-dioxo-2-naphthacenecarboxamide sulfate.

EXAMPLES 36–39

Substantially following the methods described in detail hereinabove in Examples 3 and 11, the compounds of this invention listed below in Examples 36–39 are prepared.

EXAMPLE 36

[4S-(4α,12aα)]-9-Amino-4-(dimethylamino)-7-(propylamino)-1,4,4a,5,5a,6,11,12a-octahydro-3,10,12,12a-tetrahydroxy-1,11-dioxo-2-naphthacenecarboxamide sulfate.

EXAMPLE 37

[4S-(4α,12aα)]-9-Amino-4-(dimethylamino)-7-(butylamino)-1,4,4a,5,5a,6,11,12a-octahydro-3,10,12,12a-tetrahydroxy-1,11-dioxo-2-naphthacenecarboxamide sulfate.

EXAMPLE 38

[4S-(4α,12aα)]-9-Amino-4-(dimethylamino)-7-[(2-methylpropyl)amino]-1,4,4a,5,5a,6,11,12a-octahydro-3,10,12,12a-tetrahydroxy-1,11-dioxo-2-naphthacenecarboxamide sulfate.

EXAMPLE 39

[4S-(4α,12aα) ]-9-Amino-4-(dimethylamino)-7-[(1,1-dimethylethyl)amino]-1,4,4a,5,5a,6,11,12a-octahydro-3,10,12,12a-tetrahydroxy-1,11-dioxo-2-naphthacenecarboxamide sulfate.

EXAMPLES 40–65

Substantially following the methods described in detail hereinabove in Examples 1 and 2, the compounds of this invention listed below in Examples 40–65 are prepared.

EXAMPLE 40

[4S-(4α,12aα)]-4-(Dimethylamino)-7-(methylpropylamino)-1,4,4a,5,5a,6,11,12a-octahydro-3,10,12,12a-tetrahydroxy-9-nitro-1,11-dioxo-2-naphthacenecarboxamide sulfate.

EXAMPLE 41

[4S-(4α,12aα)]-4-(Dimethylamino)-7-(butylmethylamino)-1,4,4a,5,5a,6,11,12a-octahydro-3,10,12,12a-tetrahydroxy-9-nitro-1,11-dioxo-2-naphthacenecarboxamide sulfate.

EXAMPLE 42

[4S-(4α,12aα)]-4-(Dimethylamino)-7-[(1-methylpropylamino)methylamino]-1,4,4a,5,5a,6,11,12a-octahydro-3,10,12,12a-tetrahydroxy-9-nitro-1,11-dioxo-2-naphthacenecarboxamide sulfate.

EXAMPLE 43

[4S-(4α,12aα)]-4-(Dimethylamino)-7-[(2-methylpropyl)methylamino]-1,4,4a,5,5a,6,11,12a-octahydro-3,10,12,12a-tetrahydroxy-9-nitro-1,11-dioxo-2-naphthacenecarboxamide sulfate.

EXAMPLE 44

[4S-(4α,12aα)]-4-(Dimethylamino)-7-(ethylpropylamino)-1,4,4a,5,5a,6,11,12a-octahydro-3,10,12,12a-tetrahydroxy-9-nitro-1,11-dioxo-2-naphthacenecarboxamide sulfate.

EXAMPLE 45

[4S-(4α,12aα)]-4-(Dimethylamino)-7-[(1-methylethyl)ethylamino]-1,4,4a,5,5a,6,11,12a-octahydro-3,10,12,12a-tetrahydroxy-9-nitro-1,11-dioxo-2-naphthacenecarboxamide sulfate.

EXAMPLE 46

[4S-(4α,12aα)]-4-(Dimethylamino)-7-(butylethylamino)-1,4,4a,5,5a,6,11,12a-octahydro-3,10,12,12a-tetrahydroxy-9-nitro-1,11-dioxo-2-naphthacenecarboxamide sulfate.

EXAMPLE 47

[4S-(4α,12aα)]-4-(Dimethylamino)-7-[(1-methylpropyl)ethylamino]-1,4,4a,5,5a,6,11,12a-octahydro-3,10,12,12a-tetrahydroxy-9-nitro-1,11-dioxo-2-naphthacenecarboxamide sulfate.

EXAMPLE 48

[4S-(4α,12aα)]-4-(Dimethylamino)-7-[(2-methylpropyl)ethylamino]-1,4,4a,5,5a,6,11,12a-octahydro-3,10,12,12a-tetrahydroxy-9-nitro-1,11-dioxo-2-naphthacenecarboxamide sulfate.

EXAMPLE 49

[4S-(4α,12aα)]-4-(Dimethylamino)-7-(dipropylamino)-1,4,4a,5,5a,6,11,12a-octahydro-3,10,12,12a-tetrahydroxy-9-nitro-1,11-dioxo-2-naphthacenecarboxamide sulfate.

EXAMPLE 50

[4S-(4α,12aα)]-4-(Dimethylamino)-7-[(1-methylethyl)propylamino]-1,4,4a,5,5a,6,11,12a-octahydro-3,10,12,12a-tetrahydroxy-9-nitro-1,11-dioxo-2-naphthacenecarboxamide sulfate

EXAMPLE 51

[4S-(4α,12aα)]-4-(Dimethylamino)-7-(butylpropyltetrahydroxy-9-nitro-1,11-dioxo-2-naphthacenecarboxamide sulfate.

EXAMPLE 52

[4S-(4α,12aα)]-4-(Dimethylamino)-7-[(1-methylpropyl)propylamino]-1,4,4a,5,5a,6,11,12a-octahydro-3,10,12,12a-tetrahydroxy-9-nitro-1,11-dioxo-2-naphthacenecarboxamide sulfate.

EXAMPLE 53

4S-(4α,12aα)]-4-(Dimethylamino)-7-[(2-methylpropyl)propylamino]-1,4,4a,5,5a,6,11,12a-octahydro-3,10,12,12a-tetrahydroxy-9-nitro-1,11-dioxo-2-naphthacenecarboxamide sulfate.

EXAMPLE 54

4S-(4α,12aα)]-4-(Dimethylamino)-7-[(1-methylethyl)butylamino]-1,4,4a,5,5a,6,11,12a-octahydro-3,10,12,12a-tetrahydroxy-9-nitro-1,11-dioxo-2-naphthacenecarboxamide sulfate.

EXAMPLE 55

4S-(4α,12aα)]-4-(Dimethylamino)-7-[(1-methylethyl)(1-methylpropyl)amino]-1,4,4a,5,5a,6,11,12a-octahydro-3,10,12,12a-tetrahydroxy-9-nitro-1,11-dioxo-2-naphthacenecarboxamide sulfate.

EXAMPLE 56

[4S-(4α,12aα)]-4-(Dimethylamino)-7-[(1-methylethyl)(2-methylpropyl)amino]-1,4,4a,5,5a,6,11,12a-octahydro-3,10,12,12a-tetrahydroxy-9-nitro-1,11-dioxo-2-naphthacenecarboxamide sulfate.

EXAMPLE 57

[4S-(4α,12aα)]-4-(Dimethylamino)-7-(dibutylamino)-1,4,4a,5,5a,6,11,12a-octahydro-3,10,12,12a-tetrahydroxy-9-nitro-1,11-dioxo-2-naphthacenecarboxamide sulfate.

EXAMPLE 58

[4S-(4α,12aα)]-4-(Dimethylamino)-7-[(1-methylpropyl)butylamino]-1,4,4a,5,5a,6,11,12a-octahydro-3,10,12,12a-tetrahydroxy-9-nitro-1,11-dioxo-2-naphthacenecarboxamide sulfate.

EXAMPLE 59

[4S-(4α,12aα)]-4-(Dimethylamino)-7-[(2-methylpropyl)butylamino]-1,4,4a,5,5a,6,11,12a-octahydro-3,10,12,12a-tetrahydroxy-9-nitro-1,11-dioxo-2-naphthacenecarboxamide sulfate.

EXAMPLE 60

[4S-(4α,12aα)]-4-(Dimethylamino)-7-[(1-methylpropyl)amino]-1,4,4a,5,5a,6,11,12a-octahydro-3,10,12,12a-tetrahydroxy-9-nitro-1,11-dioxo-2-naphthacenecarboxamide sulfate.

EXAMPLE 61

[4S-(4α,12aα)]-4-(Dimethylamino)-7-[(1-methylpropyl)(2-methylpropyl)amino]-1,4,4a,5,5a,6,11,12a-octahydro-3,10,12,12a-tetrahydroxy-9-nitro-1,11-dioxo-2-naphthacenecarboxamide sulfate.

EXAMPLE 62

[4S-(4α,12aα)]-4-(Dimethylamino)-7-(propylamino)-1,4,4a,5,5a,6,11,12a-octahydro-3,10,12,12a-tetrahydroxy-9-nitro-1,11-dioxo-2-naphthacenecarboxamide sulfate.

EXAMPLE 63

[4S-(4α,12aα)]-4-(Dimethylamino)-7-(butylamino)-1,4,4a,5,5a,6,11,12a-octahydro-3,10,12,12a-tetrahydroxy-9-nitro-1,11-dioxo-2-naphthacenecarboxamide sulfate.

EXAMPLE 64

[4S-(4α,12aα)]-4-(Dimethylamino)-7-[(2-methylpropyl)amino]-1,4,4a,5,5a,6,11,12a-octahydro-3,10,12,12a-tetrahydroxy-9-nitro-1,11-dioxo-2-naphthacenecarboxamide sulfate.

EXAMPLE 65

[4S-(4α,12aα)]-4-(Dimethylamino)-7-[(1,1-dimethylethyl)amino]-1,4,4a,5,5a,6,11,12a-octahydro-3,10,12,12a-tetrahydroxy-9-nitro-1,11-dioxo-2-naphthacenecarboxamide sulfate.

We claim:

1. A compound of the formula:

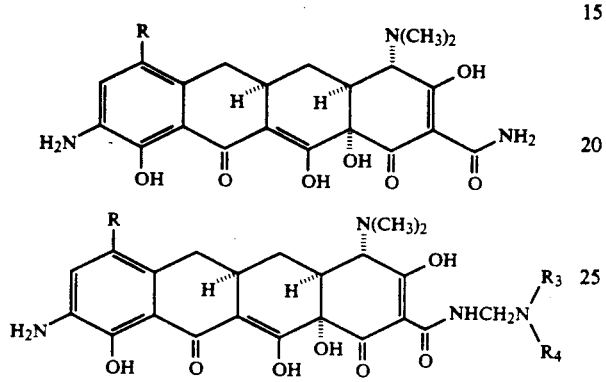

wherein: $R=NR_1R_2$, and when $R_1=$hydrogen, $R_2=$methyl, ethyl, n-propyl, 1-methylethyl, n-butyl, 1-methylpropyl, 2-methylpropyl or 1,1-dimethylethyl; and when $R_1=$methyl or ethyl, $R_2=$methyl, ethyl, n-propyl, 1-methylethyl, n-butyl, 1-methylpropyl or 2-methylpropyl; and when $R_1=$n-propyl, $R_2=$n-propyl, 1-methylethyl, n-butyl, 1-methylpropyl or 2-methylpropyl; and when $R_1=$1-methylethyl, $R_2=$n-butyl, 1-methylpropyl or 2-methylpropyl; and when $R_1=$n-butyl, $R_2=$n-butyl, 1-methylpropyl or 2-methylpropyl; and when $R_1=$1-methylethyl, $R_2=$2-methylpropyl; $R_3$ is selected from hydrogen, straight or branched $(C_1-C_3)$alkyl group; $(C_6-C_{10})$aryl group; $(C_7-C_9)$aralkyl group; or ———$(CH_2)_nCOOR_5$ when $n=1-4$ and $R_5$ is selected from hydrogen; straight or branched $(C_1-C_3)$alkyl group; or $(C_6-C_{10})$aryl group; $R_4$ is selected from hydrogen; straight or branched $(C_1-C_3)$alkyl group; $(C_6-C_{10})$aryl group; $(C_7-C_9)$aralkyl group; or —$(CH_2)_nCOOR_6$ when $n=1-4$ and $R_6$ is selected from hydrogen; straight or branched $(C_1-C_3)$alkyl; or $(C_6-C_{10})$aryl; and the pharmacologically acceptable organic and inorganic salts and metal complexes.

2. The compound according to claim 1, wherein: $R=NR_1R_2$, and when $R_1=$hydrogen, $R_2=$ethyl, n-propyl, 1-methylethyl, n-butyl, 1-methylpropyl, 2-methylpropyl or 1,1-dimethylethyl; and when $R_1=$methyl, $R_2=$methyl, ethyl, n-propyl, n-butyl, 1-methylpropyl or 2-methylpropyl; and when $R_1=$ethyl, $R_2=$ethyl, n-propyl, n-butyl, or 2-methylpropyl; and when $R_1=$n-propyl, $R_2=$n-propyl, n-butyl or 2-methylpropyl; and when $R_1=$n-butyl, $R_2=$n-butyl or 2-methylpropyl; $R_3$ is selected from straight or branched $(C_1-C_3)$alkyl group; $(C_6-C_{10})$aryl group; $(C_7-C_9)$aralkyl group; or $(CH_2)_nCOOR_5$ when $n=1-4$ and $R_5$ is selected from hydrogen; straight or branched $(C_1-C_3)$alkyl group; or $(C_6-C_{10})$aryl group; $R_4$ is selected from straight or branched $(C_1-C_3)$alkyl group; $(C_6-C_{10})$aryl group; $(C_7-C_9)$aralkyl group; or —$(CH_2)_nCOOR_6$ when $n=1-4$ and $R_6$ is selected from hydrogen; straight or branched $(C_1-C_3)$alkyl; or $(C_6-C_{10})$aryl; and the pharmacologically acceptable organic salts and metal complexes.

3. The compound according to claim 1, wherein: $R=NR_1R_2$, and when $R_1=$hydrogen, $R_2=$ethyl, n-propyl or 1-methylethyl; and when $R_1=$methyl; $R_2=$methyl, ethyl or n-propyl; and when $R_1=$ethyl; $R_2=$ethyl; $R_3$ is selected from a straight or branched $(C_1-C_3)$alkyl group; $(C_6-C_{10})$aryl group; $(C_7-C_9)$aralkyl group; or —$(CH_2)_nCOOR_5$ when $n=1-4$ and $R_5$ is selected from hydrogen; straight or branched $(C_1-C_3)$alkyl group; or $(C_6-C_{10})$aryl group; $R_4$ is selected from straight or branched $(C_1-C_3)$alkyl group; $(C_6-C_{10})$aryl group; $(C_7-C_9)$aralkyl group; or —$(CH_2)_nCOOR_6$ when $n=1-4$ $R_6$ is selected from hydrogen; straight or branched $(C_1-C_3)$alkyl; or $(C_6-C_{10})$aryl; and the pharmacological acceptable organic and inorganic salts and metal complexes.

4. A compound of the formula:

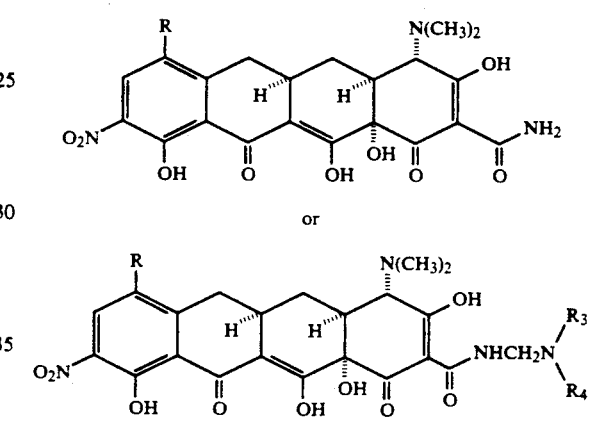

or wherein: $R=NR_1R_2$, and when $R_1=$hydrogen, $R_2=$methyl, ethyl, n-propyl, 1-methylethyl, n-butyl, 1-methylpropyl, 2-methylpropyl or 1,1-dimethylethyl; and when $R_1=$methyl or ethyl, $R_2=$methyl, ethyl, n-propyl, 1-methylethyl, n-butyl, 1-methylpropyl or 2-methylpropyl; and when $R_1=$n-propyl, $R_2=$n-propyl, 1-methylethyl, n-butyl, 1-methylpropyl or 2-methylpropyl; and when $R_1=$1-methylethyl, $R_2=$n-butyl, 1-methylpropyl or 2-methylpropyl; and when $R=$n-butyl, $R_2=$n-butyl, 1-methylpropyl or 2-methylpropyl; and when $R_1=$1-methylpropyl, $R_2=$2-methylpropyl; $R_3$ is selected from hydrogen, straight or branched $(C_1-C_3)$alkyl group; $(C_6-C_{10})$aryl group; $(C_7-C_9)$aralkyl group; or —$(CH_2)nCOOR_5$ when $n=1-4$ and $R_5$ is selected from hydrogen; straight or branched $(C_1-C_3)$alkyl group; or $(C_6-C_{10})$aryl group; $R_4$ is selected from hydrogen; straight or branched $(C_1-C_3)$alkyl group; $(D_6-C_{10})$aryl group; $(C_7-C_9)$aralkyl group; or —$(CH_2)_nCOOR_6$ when $n=1-4$ and $R_6$ is selected from hydrogen; straight or branched $(C_1-C_3)$alkyl; or $(C_6-C_{10})$aryl; and the pharmacologically acceptable organic and inorganic salts and metal complexes.

5. The compound according to claim 4, wherein $R=NR_1R_2$, and when $R_1=$hydrogen, $R_2=$ethyl, n-propyl, 1-methylethyl, n-butyl, 1-methylpropyl, 2-methylpropyl or 1,1,-dimethylethyl; and when $R_1=$methyl, $R_2=$methyl, ethyl, n-propyl, n-butyl, 1-methylpropyl, or 2-methylpropyl; and when $R_1=$ethyl, $R_2=$ethyl, n-propyl, n-butyl, or 2-methylpropyl; and when $R_1$=n-propyl, $R_2$=n-propyl, n-butyl, or 2-methylpropyl; and when $R_1$=n-butyl, $R_2$=n-butyl or 2-methylpropyl; $R_3$ is selected from straight or branched $(C_1-C_3)$alkyl group; $(C_6-C_{10})$aryl group; $(C_7-C_9)$aralkyl group; or $(CH_2)_nCOOR_5$ when n=1-4 and $R_5$ is selected from hydrogen; straight or branched $(C_1-C_3)$alkyl group; or $(C_6-C_{10})$aryl group; $R_4$ is selected from straight or branched $(C_1-C_3)$alkyl, group; $(C_6-C_{10})$aryl group; $(C_7-C_9)$aralkyl group; or —$(CH_2)_nCOOR_6$ when n=1-4 and $R_6$ is selected from hydrogen; straight or branched $(C_1-C_3)$alkyl; or $(C_6-C_{10})$aryl; and the pharmacologically acceptable organic and inorganic salts and metal complexes; $(C_1-C_3)$alkyl; $(C_6-C_{10})$aryl; and the pharmacologically acceptable organic and inorganic salts and metal complexes.

6. The compound according to claim 4, wherein: $R=NR_1R_2$, and when $R_1$=hydrogen, $R_2$=ethyl, n-propyl or 1-methylethyl; and when $R_1$=methyl, $R_2$=methyl, ethyl or n-propyl; and when $R_1$=ethyl, $R_2$=ethyl; $R_3$ is selected from a straight or branched $(C_1-C_3)$alkyl group; $(C_6-C_{10})$aryl group; $(C_7-C_9)$aralkyl group; or —$(CH_2)_nCOOR_5$ when n=1-4 and $R_5$ is selected from hydrogen; straight or branched $(C_1-C_3)$alkyl group; or $(C_6-C_{10})$aryl group; $R_4$ is selected from straight or branched $(C_1-C_3)$alkyl group; $(C_6-C_{10})$aryl group; $(C_7-C_9)$aralkyl group; or —$(CH_2)_nCOOR_6$ when n=1-4 and $R_6$ is selected from hydrogen; straight or branched $(C_1-C_3)$alkyl; or $(C_6-C_{10})$aryl; pharmacologically acceptable organic and inorganic salts and metal complexes.

7. The compound according to claim 1 wherein said inorganic salts comprise: hydrochloric, hydrobromic, hydroiodic, phosphoric, nitric or sulfate.

8. The compound according to claim 1 wherein said organic salts comprise: acetate, benzoate, citrate, cysteine or other amino acids, fumarate, glycolate, maleate, succinate, tartrate, alkylsulfonate or arylsulfonate.

9. The compound according to claim 1 wherein said metal complexes comprise: aluminum, calcium, iron, magnesium, manganese and complex salts.

10. The compound according to claim 4 wherein said inorganic salts comprise: hydrochloric, hydrobromic, hydroiodic, phosphoric, nitric or sulfate.

11. The compound according to claim 4 wherein said organic salts comprise: acetate, benzoate, citrate, cystein or other amino acids, fumarate, glycolate, maleate, succinate, tartrate, alkylsulfonate or arylsulfonate.

12. The compound according to claim 4 wherein said metal complexes comprise: aluminum, calcium, iron, magnesium, manganese and complex salts.

13. The compound according to claim 1, [4S-(4α,12aα)]-9-Amino-4,7-bis(dimethylamino)-1,4,4a,5,5a,6,11,12a-octahydro-3,10,12,12a-tetrahydroxy-1,11-dioxo-2-naphthacenecarboxamide sulfate (1:1).

14. The compound according to claim 1, [4S-(4α,12aα)]-9-Amino-4,7-bis(dimethylamino)-1,4,4a,5,5a,6,11,12a-octahydro-3,10,12,12α-tetrahydroxy-1,11-dioxo-2-naphthacenecarboxamide hydrochloride (1:1).

15. The compound according to claim 1, [4S-(4α,12aα)]-9-Amino-4,7-bis(dimethylamino)-1,4,4a,5,5a,6,11,12a-octahydro-3,10,12,12a-tetrahydroxy-1,11-dioxo-2-naphthacenecarboxamide p-toluenesulfonate (1:1).

16. The compound according to claim 1, [4S-(4α,12aα)]-9-Amino-7-(diethylamino)-4-(dimethylamino)-1,4,4a,5,5a,6,11,12a-octahydro-3,10,12,12a-tetrahydroxy-1,11-dioxo-2-naphthacenecarboxamide sulfate (1:2).

17. The compound according to claim 1, [4S-(4α,12aα)]-9-Amino-4-(dimethylamino)-7-(ethylmethylamino)-1,4,4a,5,5a,6,11,12a-octahydro-3,10,12,12a-tetrahydroxy-1,11-dioxo-2-naphthacenecarboxamide sulfate (1:1).

18. The compound according to claim 1, [4S-(4α,12aα)]-9-Amino-4-(dimethylamino)-7-[(1-methylethyl)amino]-1,4,4a,5,5a,6,11,12a-octahydro-3,10,12,12a-tetrahydroxy-1,11-dioxo-2-naphthacenecarboxamide sulfate (1:1).

19. The compound according to claim 1, [4S-(4α,12aα)]-9-Amino-4-(dimethylamino)-7-(ethylamino)-1,4,4a,5,5a,6,11,12a-octahydro-3,10,12,12a-tetrahydroxy-1,11-dioxo-2-naphthacenecarboxamide sulfate (1:1).

20. The compound according to claim 4, [4S-(4α,12aα)]-4,7-Bis(dimethylamino)-1,4,4a,5,5a,6,11,12a-octahydro-3,10,12,12a-tetrahydroxy-9-nitro-1,11-dioxo-2-naphthacenecarboxamide sulfate (1:1).

21. The compound according to claim 4, [4S-(4α,12aα)]-7-(Diethylamino)-4-(dimethylamino)-1,4,4a,5,5a,6,11,12a-octahydro-3,10,12,12a-tetrahydroxy-9-nitro-1,11-dioxo-2-naphthacenecarboxamide sulfate (1:2).

22. The compound according to claim 4, [4S-(4α,12aα)]-4-(Dimethylamino)-7-(ethylmethylamino)-1,4,4a,5,5a,6,11,12a-octahydro-3,10,12,12a-tetrahydro-9-nitro-1,11-dioxo-2-naphthacenecarboxamide sulfate (1:1).

23. The compound according to claim 4, [4S-(4α,12aα)]-4-(Dimethylamino)-7-[(1-methylethyl)-amino]-1,4,4a,5,5a,6,11,12a-octahydro-3,10,12,12a-tetrahydroxy-9-nitro-1,11-dioxo-2-naphthacenecarboxamide sulfate (1:1).

24. The compound according to claim 4, [4S-(4α,12aα)]-4-(Dimethylamino)-7-(ethylamino)-1,4,4a,5,5a,6,11,12a-octahydro-3,10,12,12a-tetrahydroxy-9-nitro-1,11-dioxo-2-naphthacenecarboxamide sulfate (1:1).

25. The compound according to claim 1, [4S-(4α,12aα)]-9-Amino-4,7-bis(dimethylamino)-1,4,4a,5,5a,6,11,12a-octahydro-3,10,12,12a-tetrahydroxy-1,11-dioxo-2-naphthacenecarboxamide.

26. The compound according to claim 1, [4S-(4α,12aα)]-9-Amino-7-(diethylamino)-4-(dimethylamino)-1,4,4a,5,5a,6,11,12a-octahydro-3,10,12,12a-tetrahydroxy-1,11-dioxo-2-naphthacenecarboxamide.

27. The compound according to claim 1, [4S-(4α,12aα)]-9-Amino-4-(dimethylamino)-7-(ethylmethylamino)-1,4,4a,5,5a,6,11,12a-octahydro-3,10,12,12a-tetrahydroxy-1,11-dioxo-2-naphthacenecarboxamide.

28. The compound according to claim 1, [4S-(4α,12aα)]-9-Amino-4-(dimethylamino)-7-[(1-methylethyl)amino]-1,4,4a,5,5a,6,11,12a-octahydro-3,10,12,12a-tetrahydroxy-1,11-dioxo-2-naphthacenecarboxamide.

29. The compound according to claim 1, [4S-(4α,12aα)]-9-Amino-4-(dimethylamino)-7-(ethylamino)-1,4,4a,5,5a,6,11,12a-octahydro-3,10,12,12a-tetrahydroxy-1,11-dioxo-2-naphthacenecarboxamide.

30. The compound according to claim 4, [4S-(4α,12aα)]-4,7-Bis(dimethylamino)-1,4,4a,5,5a,6,11,12a-octahydro-3,10,12,12a-tetrahydroxy-9-nitro-1,11-dioxo-2-naphthacenecarboxamide.

31. The compound according to claim 4, [4S-(4α,12aα)]-7-(Diethylamino)-4-(dimethylamino)-1,4,4a,5,5a,6,11,12a-octahydro-3,10,12,12a-tetrahydroxy-9-nitro-1,11-dioxo-2-naphthacenecarboxamide.

32. The compound according to claim 4, [4S-(4α,1-2aα)]-4-(Dimethylamino)-7-(ethylmethylamino)-1,4,4a,5,5a,6,11,12a-octahydro-3,10,12,12a-tetrahydro-9-nitro-1,11-dioxo-2-naphthacenecarboxamide.

33. The compound according to claim 4, [4S-(4α,1-2aα)]-4-(Dimethylamino)-7-[(1-methylethyl)amino]-1,4,4a,5,5a,6,11,12a-octahydro-3,10,12,12a-tetrahydroxy-9-nitro-1,11-dioxo-2-naphthacenecarboxamide.

34. The compound according to claim 4, [4S-(4α,1-2aα)]-4-(Dimethylamino)-7-(ethylamino)-1,4,4a,5-,5a,6,11,12a-octahydro-3,10,12,12a-tetrahydroxy-9-nitro-1,11-dioxo-2-naphthacenecarboxamide.

35. A method for the prevention, treatment or control of bacterial infections in warm-blooded animals which comprises administering to said animal a pharmacologically effective amount of a compound according to claim 1.

36. A pharmaceutical composition of matter comprising a compound according to claim 1 in association with a pharmaceutically acceptable carrier.

37. A veterinary composition which comprises a pharmacologically effective amount of a compound according to claim 1 and pharmaceutically acceptable carrier.

38. A method for the prevention, treatment or control of bacterial infections in warm-blooded animals caused by bacteria having the TetM and TetK resistant determinants which comprises administering to said animal a pharmacologically effective amount of a compound according to claim 1.

39. An antibacterial pharmaceutical composition of matter comprising an effective amount of a compound according to claim 1 and an effective amount of an antioxidant in association with a pharmaceutically acceptable carrier.

40. The composition of claim 39 wherein said antioxidant comprises: cysteine, cysteine hydrochloride, dithiothreitol, ascorbic acid, monothioglycerol or thioglycolic acid.

* * * * *